United States Patent
Aizenman et al.

(10) Patent No.: US 9,932,382 B2
(45) Date of Patent: Apr. 3, 2018

(54) KV2.1 CHANNEL-DERIVED PEPTIDES AND METHODS OF USE

(71) Applicant: University of Pittsburgh—Of the Commonwealth System of Higher Education, Pittsburgh, PA (US)

(72) Inventors: Elias Aizenman, Pittsburgh, PA (US); Meghan McCord, Pittsburgh, PA (US)

(73) Assignee: University of Pittsburgh—Of The Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 15/126,966

(22) PCT Filed: Mar. 17, 2015

(86) PCT No.: PCT/US2015/020932
§ 371 (c)(1),
(2) Date: Sep. 17, 2016

(87) PCT Pub. No.: WO2015/142826
PCT Pub. Date: Sep. 24, 2015

(65) Prior Publication Data
US 2017/0174740 A1    Jun. 22, 2017

Related U.S. Application Data

(60) Provisional application No. 61/968,501, filed on Mar. 21, 2014.

(51) Int. Cl.
*C07K 14/005* (2006.01)
*C07K 14/705* (2006.01)

(52) U.S. Cl.
CPC .......... *C07K 14/705* (2013.01); *C07K 14/005* (2013.01); *C07K 2319/10* (2013.01)

(58) Field of Classification Search
None
See application file for complete search history.

(56) References Cited

PUBLICATIONS

Chauhan A. et al., "The Taming of the Cell Penetrating Domain of the HIV Tag: Myths and Realities," *Journal of Controlled Release*, 117(2):148-162, 2007.

Feinshreiber L. et al., "Non-conducting function of the Kv2.1 channel enables it to recruit vesicles for release in neuroendocrine and nerve cells," *J Cell Sci*, 123:1940-1947, 2010.

International Search Report and Written Opinion of the International Searching Authority, dated May 4, 2015, for corresponding International Application No. PCT/US2015/020932, 10 pages.

McCord M. C. and Aizenman E., "Convergent Ca2+ and Zn2+ signaling regulates apoptotic Kv2.1 K+ currents," *Proc. Natl. Acad. Sci. USA*, 110(34):13988-13993, 2013.

McCord M. C. et al., "Syntaxin-binding domain of Kv2.1 is essential for the expression of apoptotic K+ currents," *The Journal of Physiology*, 592(16):3511-3521, 2014.

Norris et al., "Regulation of Neuronal Proapoptotic Potassium Currents by the Hepatitis C Virus Nonstructural Protein 5A," *The Journal of Neuroscience*, 32(26):8865-8870, 2012.

Shah N. H. and Aizenman E., "Voltage-gated potassium channels at the crossroads of neuronal function, ischemic tolerance, and neurodegeneration," *Translational Stroke Research*, 5(1):38-58, 2014.

Singer-Lahat D. et al., "Direct Interaction of Endogenous Kv Channels with Syntaxin Enhances Exocytosis by Neuroendocrine Cells," *PLoS One*, 3(1):e1381, 2008.

Singer-Lahat D. et al., "K+ Channel Facilitation of Exocytosis by Dynamic Interaction with Syntaxin," *The Journal of Neuroscience*, 27(7):1651-1658, 2007.

Tsuk S. et al., "Kv2.1 Channel Activation and Inactivation Is Influenced by Physical Interactions of Both Syntaxin 1A and the Syntaxin 1A/Soluble N-Ethylmaleimide-Sensitive Factor-25 (t-SNARE) Complex with the C Terminus of the Channel," *Molecular Pharmacology*, 67(2):480-488, 2005.

*Primary Examiner* — John D Ulm
(74) *Attorney, Agent, or Firm* — Klarquist Sparkman, LLP

(57) ABSTRACT

Peptides capable of interfering with the Kv2.1-mediated apoptotic $K^+$ current surge that leads to neuronal cell death are described. The disclosed peptides are derived from the C-terminal region of Kv2.1, which mediates binding to the SNARE protein syntaxin. Disruption of Kv2.1 binding to syntaxin inhibits the apoptotic $K^+$ current surge that leads to neuronal cell death. The present disclosure provides methods of inhibiting binding of Kv2.1 to syntaxin in a cell (in vitro or in vivo), such as for neuroprotection following cerebral ischemia, stroke, or traumatic brain injury, or during the course of a neurodegenerative disease, or any other condition associated with neuronal cell death.

20 Claims, 12 Drawing Sheets

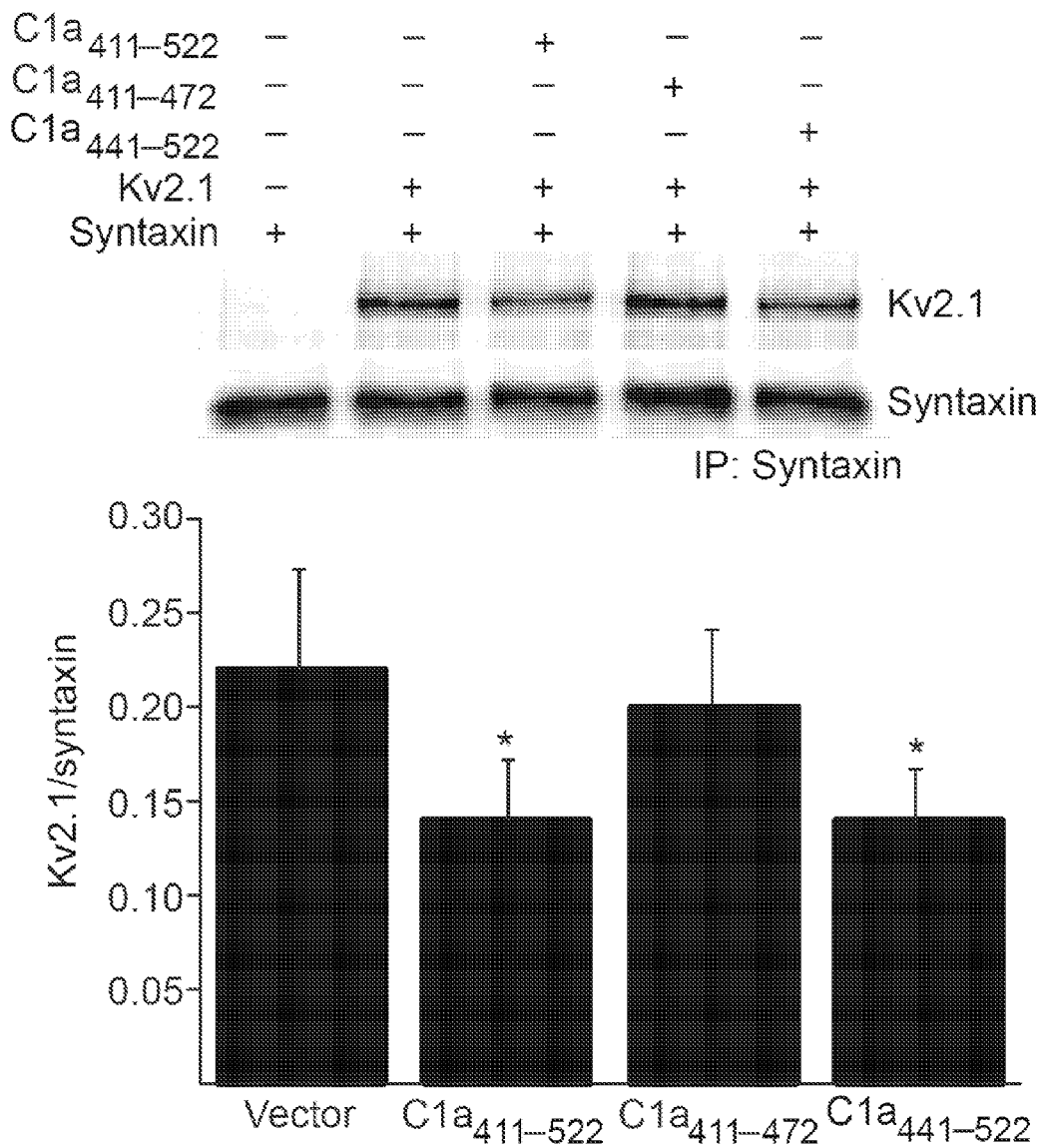

FIG. 7

Rat Kv2.1 – SEQ ID NO: 3

```
  1  mtkhgsrsts slpppepmeiv rskacsrrvr lnvgglahev lwrtldrlpr trlgklrdcn
 61  thdsllqvcd dysledneyf fdrhpgafts ilnfyrtgrl hmmeemcals fsqeldywgi
121  deiylesccq aryhqkkeqm neelkreaet lreregeefd ntccaekrkk lwdllekpns
181  svaakilaii simfivlsti alslntlpel qsldefgqst dnpqlahvea vciawftmey
241  llrflsspkk wkffkgplna idllailpyy vtifltesnk svlqfqnvrr vvqifrimri
301  lrilklarhs tglqslgftl rrsynelgll ilflamgimi fsslvffaek deddtkfksi
361  pasfwwatit mttvgygdiy pktllgkivg glcciagvlv ialpipiivn nfsefykeqk
421  rqekaikrre alerakrngs ivsmnmkdaf arsiemmdiv vekngesiak kdkvqdnhls
481  pnkwkwtkra lsetsssksf etkeqgspek arssssspqhl nvqqledmys kmaktqsqpi
541  lntkemapqs kppeelemss mpspvaplpa rtegvidmrs mssidsfisc atdfpeatrf
601  shsplaslss kagsstapev gwrgalgasg grltetnpip etsrsgffve sprssmktnn
661  plklralkvn fvegdptpll pslglyhdpl rnrggaaaav aglecaslld kpvlspessi
721  yttasartpp rspekhtaia fnfeagvhhy idtdtddegg llysvdsspp kslhgstspk
781  fstgartekn hfessplpts pkflrpncvy sseglgtkgp gaqekcklen htppdvhmlp
841  gggahgstrd qsi
```

KV2.1 CHANNEL-DERIVED PEPTIDES AND METHODS OF USE

CROSS REFERENCE TO RELATED APPLICATIONS

This is the U.S. National Stage of International Application No. PCT/US2015/020932, filed Mar. 17, 2015, which was published in English under PCT Article 21(2), which in turn claims the benefit of U.S. Provisional Application No. 61/968,501, filed Mar. 21, 2014, which is herein incorporated by reference in its entirety.

ACKNOWLEDGMENT OF GOVERNMENT SUPPORT

This invention was made with government support under grant number NS043277 awarded by the National Institutes of Health. The government has certain rights in the invention.

FIELD

This disclosure concerns peptides that interfere with binding of potassium channel Kv2.1 to syntaxin and their use, such as for neuroprotection following cerebral ischemia or central nervous system trauma.

BACKGROUND

Potassium is the most abundant intracellular cation in neurons. It is essential for maintaining the resting membrane potential and also for regulating cellular volume (Pasantes-Morales et al., *J Neurosci Res* 34, 219-224, 1993; Yu, *Prog Neurobiol* 70, 363-386, 2003). During injury, $K^+$ efflux and intracellular $K^+$ loss critically contribute to the apoptotic volume decrease (Bortner et al., *J Biol Chem* 272, 32436-32442, 1997; Maeno et al., *Proc Natl Acad Sci USA* 97, 9487-9492, 2000; Lang and Hoffmann, *Compr Physiol* 2, 2037-2061, 2012), a hallmark morphological feature of programmed cell death (Kerr et al., *Br J Cancer* 26, 239-257, 1972). In addition, reduced cytosolic $K^+$ enables apoptosis by providing a permissive environment for activation of caspases and nucleases (Hughes et al., *J Biol Chem* 272, 30567-30576, 1997; Yu et al., *Science* 278, 114-117, 1997). Kv2.1, a voltage-dependent delayed-rectifier $K^+$ channel normally involved in the regulation of high-frequency repetitive firing (Pongs, *FEBS Lett* 452, 31-35, 1999; Du et al., *J Physiol* 522, 19-31, 2000; Guan et al., *J Physiol* 591, 4807-4825, 2013), acts as the primary conduit for $K^+$ efflux during apoptotic cell death in neocortical and hippocampal neurons (Pal et al., *J Neurosci* 23, 4798-4802, 2003; Shen et al., *J Neurosci Res* 87, 3153-3160, 2009). This process occurs via a syntaxin-dependent exocytotic incorporation of new Kv2.1-encoded channels into the plasma membrane of dying neurons, measurable as a large enhancement of voltage-dependent $K^+$ currents (McLaughlin et al., *J Neurosci* 21, 3303-3311, 2001; Pal et al., *J Neurosci* 23, 2003; Pal et al., *Cell Death Differ* 13, 661-667, 2006). Inhibiting any of the upstream signaling events leading to the insertion of Kv2.1, or blocking Kv2.1 channel function itself, is neuroprotective (Yu et al., *Science* 278, 114-117, 1997; McLaughlin et al., *J Neurosci* 21, 3303-3311, 2001; Pal et al., *J Neurosci* 23, 4798-4802, 2003; Aras and Aizenman, *Antioxid Redox Signal* 15, 2249-63, 2011).

SUMMARY

Isolated or recombinant Kv2.1 polypeptides capable of disrupting binding of Kv2.1 to syntaxin, and their use (such as for neuroprotection) are provided by the present disclosure. In some embodiments, the Kv2.1 polypeptides are derived from the C1a peptide of a Kv2.1 protein, such as a C1a peptide set forth herein as SEQ ID NO: 2, SEQ ID NO: 4, SEQ ID NO: 6 or SEQ ID NO: 7. In some examples, the Kv2.1 polypeptide comprises the peptide of SEQ ID NO: 9, or a conservative variant thereof. Fusion proteins comprising the Kv2.1 polypeptides and a heterologous protein, such as a cell-penetrating protein (CPP), are also provided. Further provided are compositions comprising a Kv2.1 polypeptide or fusion protein, and a pharmaceutically acceptable carrier.

Nucleic acid molecules and vectors comprising the Kv2.1 polypeptides and fusion proteins disclosed herein are further provided by the present disclosure.

Methods of inhibiting binding of syntaxin to Kv2.1 in a cell are also provided herein. In some embodiments, the method includes contacting the cell with a polypeptide, fusion protein, composition, nucleic acid molecule or vector disclosed herein.

Methods of inhibiting neuronal damage in a subject are further provided. In some embodiments, the method includes administering to the subject a polypeptide, fusion protein, composition, nucleic acid molecule or vector disclosed herein.

The foregoing and other features and advantages will become more apparent from the following detailed description of several embodiments, which proceeds with reference to the accompanying figures.

BRIEF DESCRIPTION OF THE DRAWINGS

(FIG. 1A) Representative whole-cell $K^+$ currents and pooled mean±SEM current densities recorded from Kv2.1-expressing Chinese hamster ovary (CHO) cells without (n=19) or with (n=11) 30 µM 2,2'-dithiodipyridine (DTDP), Kv2.1ΔC1a-expressing CHO cells without (n=10) or with (n=10) 30 µM DTDP, or CHO cells expressing a 1:1 ratio of Kv2.1 and Kv2.1ΔC1a without (n=9) or with (n=16) 30 µM DTDP. Results show that the increase in $K^+$ currents triggered by DTDP is suppressed in CHO cells expressing Kv2.1ΔC1a. Currents were evoked by a series voltage steps from −80 mV to +80 mV in 10 mV increments. To determine current density values, steady-state current amplitudes were measured 180 msec after the initiation of the +10 mV step and normalized to cell capacitance. Scale bars: 3 nA, 25 msec; **p<0.01, ANOVA/Dunnett. (FIG. 1B) Mean±SEM IV curves of CHO cells expressing Kv2.1 or Kv2.1ΔC1a show that upon depolarization, Kv2.1 mutants lacking their C1a domain exhibit similar $K^+$ currents as WT Kv2.1 channels.

(FIG. 2A) Representative whole-cell $K^+$ currents and pooled mean±SEM current densities recorded from untransfected neurons without (n=10) or with (n=8) 30 µM DTDP, and from C1a-expressing neurons without (n=8) or with (n=9) 30 µM DTDP. Currents were evoked by a series voltage steps from −80 mV to +80 mV in 10 mV increments. To determine current density values, steady-state current amplitudes were measured 180 msec after the initiation of the +10 mV step and normalized to cell capacitance. Scale bars: 5 nA, 25 msec; **p<0.01, ANOVA/Dunnett. (FIG. 2B) Mean±SEM IV curves of untransfected and C1a-expressing neurons demonstrate that the peptide does not significantly alter K⁺ currents when compared to control cells.

FIGS. 3A-3B: Kv2.1/syntaxin binding is disrupted by C1a peptides. (FIG. 3A) Representative co-immunoprecipitation and quantified results from syntaxin-expressing CHO cells co-transfected with Kv2.1, in addition to C1a, $C1a_{411-472}$, or $C1a_{141-522}$. Following syntaxin immunoprecipitation, blots were probed with antibodies against Kv2.1 or syntaxin (n=6; *p<0.05, ANOVA/Bonferroni). (FIG. 3B) $C1a_{441-522}$ prevents Kv2.1/syntaxin binding in the presence of Src kinase, which was previously shown to enhance this interaction (McCord and Aizenman, *Proc Natl Acad Sci USA* 110, 13988-13993, 2013). Representative co-immunoprecipitation and quantified results from syntaxin-expressing CHO cells co-transfected with Kv2.1 and Src in the absence or presence of $C1a_{441-522}$. Following syntaxin immunoprecipitation, blots were probed with antibodies against Kv2.1 or syntaxin (n=6; *p<0.05, paired t-test).

(FIG. 6A) Resting membrane potential (Vm) and input resistance ($R_{in}$) were measured under current clamp, and threshold synaptic conductance (Thresh-$g_{syn}$) was measured under dynamic clamp in neurons expressing an empty vector or $C1a_{441-522}$ (mean±SEM; n=23-28 cells per group). (FIG. 6B) Repetitive firing was recorded in vector- or $C1a_{441-522}$-expressing neurons using 1 sec depolarization current steps of increasing amplitude from 15-120 pA. Representative traces of neurons from each group at three depolarizing currents, and mean±SEM frequency-current relationships at eight separate currents (*p<0.05, t-test between vector- and $C1a_{441-522}$-expressing neurons; n=23-28 cells per group. Scale bars: 20 mV, 500 msec).

FIG. 7: The amino acid sequence of rat Kv2.1 (SEQ ID NO: 3). The underlined region was scanned to generate 76 peptides that overlap by one amino acid. The nine amino acid sequence (SEQ ID NO: 9) shown in bold underline was identified as the minimal syntaxin-binding domain.

SEQUENCE LISTING

Figure 1A:
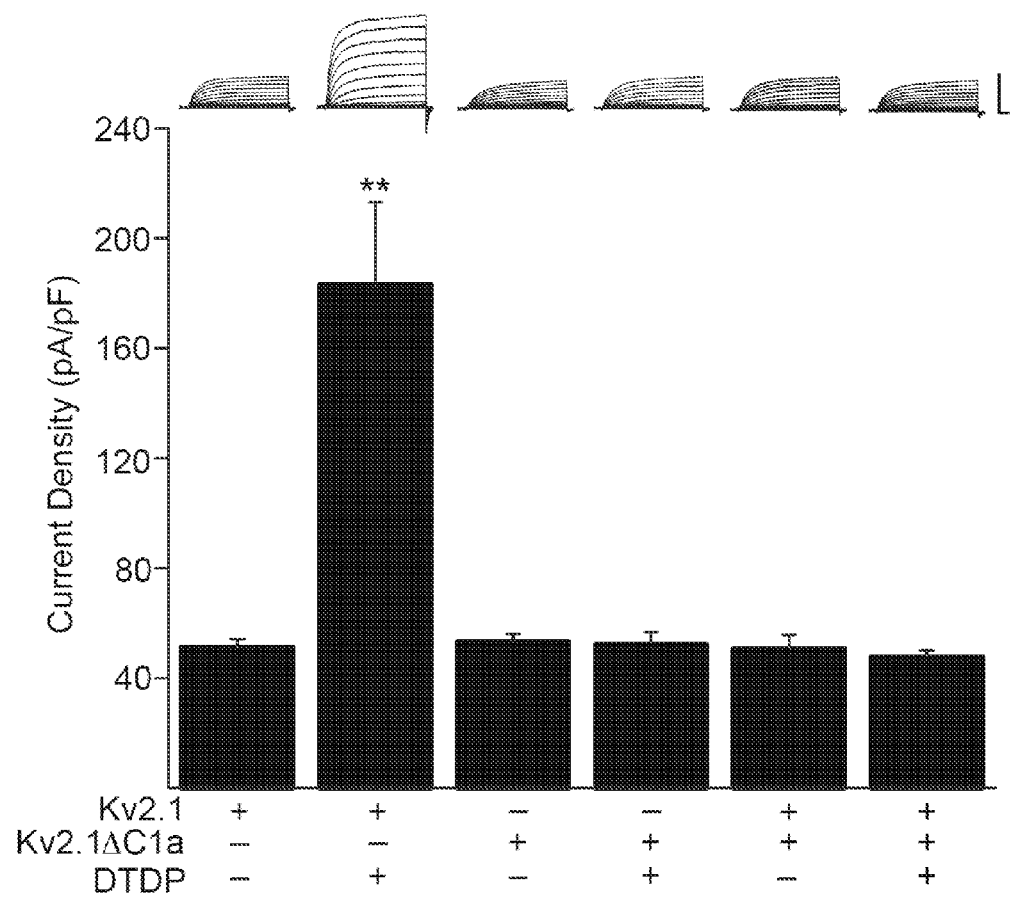
FIGS. 1A-1B: The syntaxin-binding C1a domain of Kv2.1 is required for expression of the apoptotic $K^+$ current enhancement.

The amino acid sequences listed in the accompanying sequence listing are shown using standard three letter code for amino acids, as defined in 37 C.F.R. 1.822. The Sequence Listing is submitted as an ASCII text file, created on Sep. 6, 2016, 26.5 KB, which is incorporated by reference herein. In the accompanying sequence listing:

SEQ ID NO: 1 is the amino acid sequence of human Kv2.1, deposited under GENBANK™ Accession No. NP_004966.1.

SEQ ID NO: 2 is the amino acid sequence of a human Kv2.1 C1a peptide.

SEQ ID NO: 3 is the amino acid sequence of rat Kv2.1, deposited under GENBANK™ Accession No. NP_037318.1.

SEQ ID NO: 4 is the amino acid sequence of a rat Kv2.1 C1a peptide.

SEQ ID NO: 5 is the amino acid sequence of mouse Kv2.1, deposited under GENBANK™ Accession No. NP_032446.2.

SEQ ID NO: 6 is the amino acid sequence of a mouse Kv2.1 C1a peptide.

SEQ ID NO: 7 is the amino acid consensus sequence of human, rat and mouse Kv2.1 C1a peptides.

SEQ ID NO: 8 is the amino acid sequence of the HIV-1 TAT peptide.

SEQ ID NO: 9 is the amino acid sequence of a minimal syntaxin-binding domain of Kv2.1.

DETAILED DESCRIPTION

I. Abbreviations

BAF butoxy-carbonyl-aspartate-fluoromethyl ketone
CHO Chinese hamster ovary
CNS central nervous system
CPP cell-penetrating peptide
DRG dorsal root ganglia
DTDP 2,2'-dithiodipyridine
eGFP enhanced green fluorescent protein
GFP green fluorescent protein
HW human immunodeficiency virus
MCAO middle cerebral artery occlusion
$R_{in}$ input resistance
SDS sodium dodecyl sulfate
SEM standard error of the mean
SNARE N-ethylmaleimide-sensitive factor attachment protein receptor
TBI traumatic brain injury
Vm membrane potential (Vm)
WT wild type

II. Terms and Methods

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Administer: As used herein, administering a composition (e.g. a polypeptide) to a subject means to give, apply or bring the composition into contact with the subject. Administration can be accomplished by any of a number of routes, such as, for example, intravenous, intrathecal, topical, oral, subcutaneous, intramuscular, intranasal, intraperitoneal, intramuscular or by direct injection into a tissue.

Cell-penetrating peptide (CPP): Peptides that facilitate the cellular uptake of another protein or molecular cargo linked by a covalent bond or non-covalent interaction. CPPs generally deliver cargo into a cell by endocytosis. In many instances, CPPs have an amino acid composition that is rich in charged amino acids, such as lysine or arginine, or have sequences that contain an alternating pattern of polar/charged amino acids and non-polar/hydrophobic amino acids.

Cerebral ischemia or ischemic stroke: A condition that occurs when an artery to or in the brain is partially or completely blocked such that the oxygen demand of the tissue exceeds the oxygen supplied. Deprived of oxygen and other nutrients following an ischemic stroke, the brain suffers damage as a result of the stroke.

Ischemic stroke can be caused by several different kinds of diseases. The most common problem is narrowing of the arteries in the neck or head. This is most often caused by atherosclerosis, or gradual cholesterol deposition. If the arteries become too narrow, blood cells may collect in them and form blood clots (thrombi). These blood clots can block the artery where they are formed (thrombosis), or can dislodge and become trapped in arteries closer to the brain (embolism).

Another cause of stroke is blood clots in the heart, which can occur as a result of irregular heartbeat (for example, atrial fibrillation), heart attack, or abnormalities of the heart valves. While these are the most common causes of ischemic stroke, there are many other possible causes. Examples include use of street drugs, traumatic injury to the blood vessels of the neck, or disorders of blood clotting.

Ischemic stroke is by far the most common kind of stroke, accounting for about 80% of all strokes. Stroke can affect people of all ages, including children. Many people with ischemic strokes are older (60 or more years old), and the risk of stroke increases with older ages. At each age, stroke is more common in men than women, and it is more common among African-Americans than white Americans. Many people with stroke have other problems or conditions which put them at higher risk for stroke, such as high blood pressure (hypertension), heart disease, smoking, or diabetes.

Contacting: Placement in direct physical association; includes both in solid and liquid form.

Fusion protein: A protein containing amino acid sequence from at least two different (heterologous) proteins or peptides. In some examples herein, the fusion protein comprises a portion of a Kv2.1 protein and a cell-penetrating peptide. Fusion proteins can be generated, for example, by expression of a nucleic acid sequence engineered from nucleic acid sequences encoding at least a portion of two different (heterologous) proteins. To create a fusion protein, the nucleic acid sequences must be in the same reading frame and contain no internal stop codons. Fusion proteins, particularly short fusion proteins, can also be generated by chemical synthesis.

Heterologous: A heterologous protein or polypeptide refers to a protein or polypeptide derived from a different source or species.

Ischemia: A vascular phenomenon in which a decrease in the blood supply to a bodily organ, tissue, or part is caused, for instance, by constriction or obstruction of one or more blood vessels. Ischemia sometimes results from vasoconstriction or thrombosis or embolism. Ischemia can lead to direct ischemic injury, tissue damage due to cell death caused by reduced oxygen supply.

Isolated: An "isolated" biological component (such as a nucleic acid molecule, protein, or cell) has been substantially separated or purified away from other biological components in the cell, blood or tissue of the organism, or the organism itself, in which the component naturally occurs, such as other chromosomal and extra-chromosomal DNA and RNA, proteins and cells. Nucleic acid molecules and proteins that have been "isolated" include those purified by standard purification methods. The term also embraces nucleic acid molecules and proteins prepared by recombinant expression in a host cell as well as chemically synthesized nucleic acid molecules and proteins.

Kv2.1: A voltage-dependent delayed-rectifier $K^+$ channel belonging to the 6-transmembrane family of potassium channels. The pore-forming alpha subunits contain a single pore-forming region and combine to form tetramers. Heterotrimeric channels can be formed within subfamilies (e.g., Kv1.1 with Kv1.2). Kv2.1 is involved in the regulation of high-frequency repetitive firing (Pongs, *FEBS Lett* 452, 31-35, 1999; Du et al., *J Physiol* 522, 19-31, 2000; Guan et al., *J Physiol* 591, 4807-4825, 2013), and acts as the primary conduit for $K^+$ efflux during apoptotic cell death in neocortical and hippocampal neurons (Pal et al., *J Neurosci* 23, 4798-4802, 2003; Shen et al., *J Neurosci Res* 87, 3153-3160, 2009).

Kv2.1 peptide (or Kv2.1 polypeptide): A peptide or polypeptide derived from a Kv2.1 protein, such as a human, rat or mouse Kv2.1 protein. The Kv2.1 polypeptides disclosed herein can be isolated Kv2.1 polypeptides or recombinant polypeptides based on the sequence of (or sequence similarity with) a Kv2.1 polypeptide. The amino acid sequences of human, rat and mouse Kv2.1 proteins are set forth herein as SEQ ID NO: 1, SEQ ID NO: 3 and SEQ ID NO: 5, respectively. A C1a peptide or C1a polypeptide refers to a peptide or polypeptide derived from the most proximal C-terminal C1a region of a Kv2.1 protein, such as a human, rat or mouse Kv2.1 protein. C1a peptides from human, rat and mouse are set forth herein as SEQ ID NO: 2, SEQ ID NO: 4 and SEQ ID NO: 6, respectively. A human/rat/mouse C1a peptide consensus sequence is set forth herein as SEQ ID NO: 7. As disclosed herein, a Kv2.1 (or C1a) peptide or polypeptide is generally about 8 to about 60 amino acids in length, such as about 8 to about 50, about 10 to about 40, about 10 to about 30, about 12 to about 20, about 8 to about 20, or about 10 to about 15 amino acids in length. Kv2.1 peptides include variants of the above-listed sequences, such as variants having at least 85%, 90%, 95%, 96%, 97%, 98% or 99% identity to any of the above-listed sequences or portion thereof, or variants having no more than 5, no more than 4, no more than 3, no more than 2 or no more than 1 conservative amino acid substitution(s).

Neurodegenerative disorder or disease: Refers to any type of disorder or disease that is associated with a progressive loss of motor, sensory and/or perceptual functions, and often involves behavioral and cognitive deficits. Neurodegenerative diseases are typically characterized by the progressive loss of structure or function of neurons, such as neurons within the cerebral cortex, basal ganglia, cerebellum, brain stem or motor systems. Neurodegenerative disorders include, but are not limited to, Alzheimer's disease, Parkinson's disease, Huntington's disease, ALS, multiple sclerosis, Lewy body dementia, vascular dementia, progressive supranuclear palsy, corticobasal degeneration, multiple system atrophy and frontotemporal dementia.

Neuronal damage: Damage to the neurons, such as the neurons of the CNS. In particular embodiments herein, the neuronal damage is in the brain. Neuronal damage can be caused by a variety of conditions and events, such as ischemic stroke, hemorrhagic stroke or brain injury, such as traumatic brain injury. In some examples of the present disclosure, the neuronal damage is caused by an acute condition, such as a stroke.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carriers: The pharmaceutically acceptable carriers useful in the methods disclosed herein are conventional. *Remington's Pharmaceutical Sciences*, by E. W. Martin, Mack Publishing Co., Easton, Pa., 15th Edition (1975), describes compositions and formulations suitable for pharmaceutical delivery of polypeptides.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain non-toxic auxiliary substances, such as wetting or emulsifying agents, preservatives, salts, amino acids, and pH buffering agents and the like, for example sodium or potassium chloride or phosphate, Tween, sodium acetate or sorbitan monolaurate.

Polypeptide or peptide: A polymer in which the monomers are amino acid residues which are joined together through amide bonds. When the amino acids are alpha-amino acids, either the L-optical isomer or the D-optical isomer can be used. The terms "polypeptide," "peptide" or "protein" as used herein are intended to encompass any amino acid sequence and include modified sequences such as glycoproteins. The terms "polypeptide" and "peptide" are specifically intended to cover naturally occurring proteins, as well as those which are recombinantly or synthetically produced. The term "residue" or "amino acid residue" includes reference to an amino acid that is incorporated into a protein, polypeptide, or peptide.

A conservative substitution in a polypeptide is a substitution of one amino acid residue in a protein sequence for a different amino acid residue having similar biochemical properties. Typically, conservative substitutions have little to no impact on the activity of a resulting polypeptide. For example, a protein or peptide including one or more conservative substitutions (for example no more than 1, 2, 3, 4 or 5 substitutions) retains the structure and function of the wild-type protein or peptide. A polypeptide can be produced to contain one or more conservative substitutions by manipulating the nucleotide sequence that encodes that polypeptide using, for example, standard procedures such as site-directed mutagenesis or PCR. In one example, such variants can be readily selected by testing antibody cross-reactivity or its ability to induce an immune response. Examples of conservative substitutions are shown below.

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Promoter: A region of DNA that directs/initiates transcription of a nucleic acid (e.g. a gene). A promoter includes necessary nucleic acid sequences near the start site of transcription. Typically, promoters are located near the genes they transcribe. A promoter also optionally includes distal enhancer or repressor elements that can be located as much as several thousand base pairs from the start site of transcription.

Purified: The term purified does not require absolute purity; rather, it is intended as a relative term. Thus, for example, a purified peptide preparation is one in which the peptide or protein is more enriched than the peptide or protein is in its natural environment within a cell. In one embodiment, a preparation is purified such that the protein or peptide represents at least 50% of the total peptide or protein content of the preparation. Substantial purification denotes purification from other proteins or cellular components. A substantially purified protein is at least 60%, 70%, 80%, 90%, 95% or 98% pure. Thus, in one specific, non-limiting example, a substantially purified protein is 90% free of other proteins or cellular components.

Recombinant: A recombinant nucleic acid or protein is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques. The term recombinant includes nucleic acids and proteins that have been altered solely by addition, substitution, or deletion of a portion of a natural nucleic acid molecule or protein.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

Stroke: The sudden death of brain cells due to a lack of oxygen when the blood flow to the brain is impaired by blockage or rupture of an artery to the brain. Ischemic stroke refers to a condition that occurs when an artery to or in the brain is partially or completely blocked such that the oxygen demand of the tissue exceeds the oxygen supplied. Deprived of oxygen and other nutrients following an ischemic stroke, the brain suffers damage as a result of the stroke. Ischemic stroke can be caused by several different kinds of diseases. The most common problem is narrowing of the arteries in the neck or head. This is most often caused by atherosclerosis, or gradual cholesterol deposition. If the arteries become too narrow, blood cells may collect in them and form blood clots (thrombi). These blood clots can block the artery where they are formed (thrombosis), or can dislodge and become trapped in arteries closer to the brain (embolism).

Another cause of ischemic stroke is blood clots in the heart, which can occur as a result of irregular heartbeat (for example, atrial fibrillation), heart attack, or abnormalities of the heart valves. While these are the most common causes of ischemic stroke, there are many other possible causes. Examples include use of street drugs, traumatic injury to the blood vessels of the neck, or disorders of blood clotting.

Ischemic stroke is by far the most common kind of stroke, accounting for about 80% of all strokes. Hemorrhagic stroke is another kind of stroke that results from an accumulation of blood in or around the brain, such as from a ruptured blood vessel. Hemorrhages in the brain can be caused by a variety of disorders that affect the blood vessels, such as long-term high blood pressure and cerebral aneurysms (a week or thin spot on a blood vessel wall).

Subject: Living multi-cellular vertebrate organisms, a category that includes both human and veterinary subjects, including human and non-human mammals (including research subjects such as rodents). A subject is also referred to herein as a "patient."

Syntaxin: A membrane-integrated SNARE protein that participates in exocytosis.

Synthetic: Produced by artificial means in a laboratory, for example a synthetic polypeptide can be chemically synthesized in a laboratory.

Therapeutically effective amount: A dose sufficient to prevent advancement of a disease, or to cause regression of the disease, or which is capable of reducing symptoms caused by the disease, such as cerebral ischemia.

Traumatic brain injury (TBI): A form of acquired brain injury that occurs when a sudden trauma causes damage to the brain. TBI can result when the head suddenly and violently hits an object, or when an object pierces the skull and enters brain tissue. Symptoms of a TBI can be mild, moderate, or severe, depending on the extent of the damage to the brain. A person with a mild TBI may remain conscious or may experience a loss of consciousness for a few seconds or minutes. Other symptoms of mild TBI include headache, confusion, lightheadedness, dizziness, blurred vision or tired eyes, ringing in the ears, bad taste in the mouth, fatigue or lethargy, a change in sleep patterns, behavioral or mood changes, and trouble with memory, concentration, attention, or thinking. A person with a moderate or severe TBI may show these same symptoms, but may also have a headache that gets worse or does not go away, repeated vomiting or nausea, convulsions or seizures, an inability to awaken from sleep, dilation of one or both pupils of the eyes, slurred speech, weakness or numbness in the extremities, loss of coordination, and increased confusion, restlessness, or agitation.

Vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An expression vector is a vector that contains the necessary regulatory sequences to allow transcription and translation of inserted gene or genes.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

Described herein are peptides capable of interfering with the Kv2.1-mediated apoptotic $K^+$ current surge that leads to neuronal cell death. Disclosed are peptides derived from the proximal C-terminal region of Kv2.1 (C1a), which mediates binding to the SNARE protein syntaxin. Disruption of Kv2.1 binding to syntaxin inhibits the apoptotic $K^+$ current surge that leads to neuronal cell death.

Provided herein are isolated or recombinant Kv2.1 polypeptides comprising an amino acid sequence derived from the C1a region of a Kv2.1 protein. In some embodiments, the Kv2.1 polypeptide is about 4 to about 60 amino acids in length, such as about 8 to about 60 amino acids in length, such as about 8 to about 50, about 10 to about 40, about 10 to about 30, about 8 to about 20, about 12 to about 20, or about 10 to about 15 amino acids in length, and comprising at least 8 consecutive amino acids of a Kv2.1 protein, such as a Kv2.1 protein set forth herein as any one of SEQ ID NOs: 1-7 and 9. In particular examples, the Kv2.1 polypeptide is 8, 9, 10, 11, 12, 13, 14, 15, 16, 17, 18, 19 or 20 amino acids in length and comprises at least 8, 9, 10, 11, 12, 13, 14, 15, 16, 17, 18, 19 or 20 consecutive amino acids of a C1a peptide, such as a C1a peptide set forth herein as SEQ ID NO: 2, SEQ ID NO: 4, SEQ ID NO: 6 or SEQ ID NO: 7. In specific examples, the Kv2.1 polypeptide is 8, 9, 10, 11, 12, 13, 14, 15, 16, 17, 18, 19 or 20 amino acids in length and comprises at least 8 consecutive amino acids of SEQ ID NO: 9. In other examples, the Kv2.1 polypeptide is 4, 5, 6, 7, 8, 9, 10, 11, 12, 13, 14, 15, 16, 17, 18, 19 or 20 amino acids in length and comprises at least 4 consecutive amino acids of SEQ ID NO: 9.

In particular embodiments, the Kv2.1 polypeptide is 8 to 20 amino acids in length, and the amino acid sequence of the polypeptide comprises at least 8 consecutive amino acids of SEQ ID NO: 7. In other particular embodiments, the Kv2.1 polypeptide is 10 to 15 amino acids in length and comprises at least 10 consecutive amino acids of SEQ ID NO: 7. In some examples, the Kv2.1 polypeptide comprises at least 8 or at least 10 consecutive amino acids of SEQ ID NO: 2, SEQ ID NO: 4, SEQ ID NO: 6 or SEQ ID NO: 9.

In some embodiments, the Kv2.1 polypeptide is 8 to 20 amino acids in length, and comprises at least 8 consecutive amino acids of residues 62-112 of SEQ ID NO: 7. In some embodiments, the Kv2.1 polypeptide is 10 to 15 amino acids in length, and comprises at least 10 consecutive amino acids of residues 62-112 of SEQ ID NO: 7. In some examples, the Kv2.1 polypeptide comprises at least 8 or at least 10 consecutive amino acids of residues 62-112 of SEQ ID NO: 2, SEQ ID NO: 4 or SEQ ID NO: 6.

In some embodiments, provided is an isolated or recombinant polypeptide comprising at least 8 consecutive amino acids of SEQ ID NO: 9, wherein the polypeptide is no more than 20 amino acids in length and shares at least 90% sequence identity with the Kv2.1 polypeptide sequence of SEQ ID NO: 7. In some examples, the polypeptide is 10 to 15 amino acids in length.

In some examples, the polypeptide shares at least 90% sequence identity with the Kv2.1 polypeptide sequence of SEQ ID NO: 2, SEQ ID NO: 4 or SEQ ID NO: 6. In particular examples, the polypeptide shares at least 95% sequence identity with the Kv2.1 polypeptide sequence of SEQ ID NO: 2, SEQ ID NO: 4 or SEQ ID NO: 6.

In some examples, the polypeptide comprises or consists of the amino acid sequence of SEQ ID NO: 9.

Also provided herein are fusion proteins comprising a Kv2.1 polypeptide disclosed herein and a heterologous protein or peptide. In some embodiments, the heterologous peptide is a peptide that promotes cellular uptake of the fusion protein, such as a cell-penetrating peptide (CPP).

CPPs are a family of polypeptides that facilitate transduction of proteins, nucleic acids or other compounds across membranes in a receptor-independent manner (Wadia and Dowdy, *Curr. Protein Pept. Sci.* 4(2):97-104, 2003). Typically, CPPs are short polycationic sequences that can facilitate cellular uptake of compounds to which they are linked into endosomes of cells.

The capacity of certain peptides to deliver proteins or nucleic acids into cells was originally described for the HIV-encoded Tat protein, which was shown to cross membranes and initiate transcription. It was then discovered that the portion of the Tat protein that was required for the transduction of the protein was only an 11 amino acid polypeptide, referred to as the Tat peptide (YGRKKRRQRRR; SEQ ID NO: 8). When fused with other proteins, the Tat peptide has been demonstrated to deliver these proteins, varying in size from 15 to 120 kDa, into cells in tissue culture (Frankel and Pabo, *Cell* 55(6):1189-93, 1988; Green and Loewenstein, *J. Gen. Microbiol.* 134(3):849-55, 1988; Vives et al., *J. Biol. Chem.* 272(25):16010-7, 1997; Yoon et al., *J. Microbiol.* 42(4):328-35, 2004; Cai et al., *Eur. J. Pharm. Sci.* 27(4):311-9, 2006).

Other known CPPs include PENETRATIN™, a 16 amino acid peptide derived from the third helix of the Drosophila Antennapedia homeobox gene (U.S. Pat. No. 5,888,762; Derossi et al., *J. Biol. Chem.* 269:10444-10450, 1994; Schwarze et al., *Trends Pharmacol. Sci.* 21:45-48, 2000); transportan, a 27 amino acid chimeric peptide comprised of 12 amino acids from the N-terminus of the neuropeptide galanin and the 14-amino acid protein mastoparan, connected via a lysine (U.S. Pat. No. 6,821,948; Pooga, *FASEB J.* 12:67-77, 1998; Hawiger, *Curr. Opin. Chem. Biol.* 3:89-94, 1999); peptides from the VP22 protein of herpes simplex virus (HSV) type 1 (Elliott et al., *Cell* 88:223-233, 1997); the UL-56 protein of HSV-2 (U.S. Patent Application Publication No. 2006/0099677); and the Vpr protein of HIV-1 (U.S. Patent Application Publication No. 2005/0287648). In addition, a number of artificial peptides also are known to function as CPPs, such as poly-arginine, poly-lysine and others (see, for example, U.S. Application Publication Nos. 2006/0106197; 2006/0024331; 2005/0287648; and 2003/0125242; Zhibao et al., *Mol. Ther.* 2:339-347, 2000; and Laus et al. *Nature Biotechnol.* 18:1269-1272, 2000).

In some examples, the CPP is the TAT peptide comprising or consisting of the amino acid sequence of SEQ ID NO: 8.

In some examples, the CPP is rich in charged amino acids, such as lysine or arginine. In other examples, the CPP contains an alternating pattern of polar/charged amino acids and non-polar/hydrophobic amino acids. In particular non-limiting examples, the CPP comprises poly-arginine, such as 6, 7, 8, 9, 10, 11 or 12 arginine residues. In other non-limiting examples, the CPP comprises poly-lysine, such as 6, 7, 8, 9, 10, 11 or 12 lysine residues.

In other embodiments, the heterologous protein or peptide is a protein tag, such as an affinity tag (for example, chitin binding protein, maltose binding protein, glutathione-S-transferase or poly-His), an epitope tag (for example, V5, c-myc, HA or FLAG) or a fluorescent tag (e.g., GFP or another well-known fluorescent protein).

Further provided herein are compositions comprising the polypeptide or fusion protein disclosed herein and a pharmaceutically acceptable carrier.

Also provided are isolated nucleic acid molecules encoding the polypeptides or fusion proteins disclosed herein. In some embodiments, the isolated nucleic acid molecule is operably linked to a promoter, such as a heterologous promoter. Vectors comprising the nucleic acid molecules are also provided by the present disclosure. Compositions comprising a nucleic acid molecule or vector disclosed herein and a pharmaceutically acceptable carrier are further provided.

Methods of inhibiting binding of syntaxin to Kv2.1 in a cell are provided herein. In some embodiments, the method includes contacting the cell with a polypeptide, fusion protein, composition, nucleic acid molecule or vector disclosed herein. The methods can be in vitro or in vivo methods. When the method is an in vivo method, contacting the cell with the polypeptide, fusion protein, composition, nucleic acid molecule or vector comprises administering the polypeptide, fusion protein, composition, nucleic acid molecule or vector to a subject.

Methods of inhibiting neuronal damage in a subject are further provided. In some embodiments, the method includes administering to the subject a polypeptide, fusion protein, composition, nucleic acid molecule or vector disclosed herein.

In some embodiments, the subject is suffering from, is likely to suffer from, or has suffered from cerebral ischemia, stroke, CNS trauma, traumatic brain injury, a neurodegenerative disease, or any other condition associated with neuronal damage and/or neuronal cell death.

IV. Kv2.1 Protein and Peptide Sequences

The amino acid sequences of human, rat and mouse Kv2.1 are provided below. Also provided are the amino acid sequences of the C-terminal C1a region of the human, rat and mouse Kv2.1.

Human Kv2.1 (GENBANK™ Accession No. NP_004966.1; SEQ ID NO: 1)

```
  1  mpagmtkhgs rstsslppep meivrskacs rrvrlnvggl ahevlwrtld rlprtrlgkl
 61  rdcnthdsll evcddysldd neyffdrhpg aftsilnfyr tgrlhmmeem calsfsqeld
121  ywgideiyle sccqaryhqk keqmneelkr eaetlrereg eefdntccae krkklwdlle
181  kpnssvaaki laiisimfiv lstialslnt lpelqsldef gqstdnpqla hveavciawf
241  tmeyllrfls spkkwkffkg plnaidllai lpyyvtiflt esnksvlqfq nvrrvvqifr
301  imrilrilkl arhstglqsl gftlrrsyne lgllilflam gimifsslvf faekdeddtk
361  fksipasfww atitmttvgy gdiypktllg kivgglccia gvlvialpip iivnnfsefy
421  keqkrqekai krrealerak rngsivsmnm kdafarsiem mdivveknge nmgkkdkvqd
481  nhlspnkwkw tkrtlsetss sksfetkeqg spekarssss pqhlnvqqle dmynkmaktq
541  sqpilntkes aaqskpkeel emesipspva plptrtegvi dmrsmssids fiscatdfpe
601  atrfshsplt slpsktggst apevgwrgal gasggrfvea npspdasqhs sffiespkss
661  mktnnplklr alkvnfmegd pspllpvlgm yhdplrnrgs aaaavaglec atlldkavls
721  pessiyttas aktpprspek htaiafnfea gvhqyidadt ddegqllysv dssppkslpg
781  stspkfstgt rseknhfess plptspkflr qnciysteal tgkgpsgqek cklenhispd
841  vrvlpgggah gstrdqsi
```

Human Kv2.1 C1a Peptide (SEQ ID NO: 2)

```
NFSEFYKEQKRQEKAIKRREALERAKRNGSIVSMNMKDAFARSIEMMDI
VVEKNGENMGKKDKVQDNHLSPNKWKWTKRTLSETSSSKSFETKEQGSP
EKARSSSSPQHLNV
```

The C1a peptide of human Kv2.1 (SEQ ID NO: 2) corresponds to residues 415-526 of full-length human Kv2.1 (SEQ ID NO: 1).

Rat Kv2.1 (GENBANK™ Accession No. NP_037318.1; SEQ ID NO: 3)

Rat Kv2.1 C1a Peptide (SEQ ID NO: 4)

```
NFSEFYKEQKRQEKAIKRREALERAKRNGSIVSMNMKDAFARSIEMMDIV
VEKNGESIAKKDKVQDNHLSPNKWKWTKRALSETSSSKSFETKEQGSPEK
ARSSSSPQHLNV
```

The C1a peptide of rat Kv2.1 (SEQ ID NO: 4) corresponds to residues 411-522 of full-length rat Kv2.1 (SEQ ID NO: 3).

```
  1  mtkhgsrsts slppepmeiv rskacsrrvr lnvgglahev lwrtldrlpr trlgklrdcn
 61  thdsllqvcd dysledneyf fdrhpgafts ilnfyrtgrl hmmeemcals fsqeldywgi
121  deiylesccq aryhqkkeqm neelkreaet lreregeefd ntccaekrkk lwdllekpns
181  svaakilaii simfivlsti alslntlpel qsldefggst dnpqlahvea vciawftmey
241  llrflsspkk wkffkgpina idllailpyy vtifltesnk svlqfqnvrr vvgifrimri
301  lrilklarhs tglqslgftl rrsynelgll ilflamgimi fsslvffaek deddtkfksi
361  pasfwwatit mttvgygdiy pktllgkivg glcciagvlv ialpipiivn nfsefykeqk
421  rgekaikrre alerakrngs ivsmnmkdaf arsiemmdiv vekngesiak kdkvqdnhls
481  pnkwkwtkra lsetsssksf etkeggspek arsssspqhl nvqqledmys kmaktqsqpi
541  lntkemapqs kppeelemss mpspvaplpa rtegvidmrs mssidsfisc atdfpeatrf
601  shsplaslss kagsstapev gwrgalgasg grltetnpip etsrsgffve sprssmktnn
661  plklralkvn fvegdptpll pslglyhdpl rnrggaaaav aglecaslld kpvlspessi
721  yttasartpp rspekhtaia fnfeagvhhy idtdddegq llysvdsspp kslhgstspk
781  fstgartekn hfessplpts pkflrpncvy sseqltgkgp gagekcklen htppdvhmlp
841  gggahgstrd qsi
```

Mouse Kv2.1 (GENBANK™ Accession No. NP_032446.2; SEQ ID NO: 5)

```
  1  mpagmtkhgs rstsslppep meivrskacs rrvrlnvggl ahevlwrtld rlprtrlgkl
 61  rdcnthdsll qvcddysled neyffdrhpg aftsilnfyr tgrlhmmeem calsfsqeld
121  ywgideiyle sccqaryhqk keqmneelkr eaetlrereg eefdntccae krkklwdlle
181  kpnssvaaki laiisimfiv lstialslnt lpelqsldef gqstdnpqla hveavciawf
241  tmeyllrfls spkkwkffkg pinaidllai lpyyvtiflt esnksvlqfq nvrrvvqifr
301  imrilrilkl arhstglqsl gftlrrsyne lgllilflam gimifsslvf faekdeddtk
361  fksipasfww atitmttvgy gdiypktllg kivgglccia gvlvialpip iivnnfsefy
421  keqkrqekai krrealerak rngsivsmnm kdafarsiem mdivveknge gvakkdkvqd
481  nhlspnkwkw tkralsetss sksfetkeqg spekarssss pqhlnvqqlq dmyskmaktq
541  sqpilntkem apqsqpqeel emgsmpspva plptrtegvi dmrsmssids fiscatdfpe
601  atrfshspla slsgksggst apevgwrgal gasggrlmet npipeasrsg ffvesprssm
661  kthnpmklra lkvnflegdp tpllpalgly hdplrnrgga aaavagleca slldkpvlsp
721  essiyttasa rtpprspekh taiafnfeag vhqyidtdtd degqllysvd ssppkslhgs
781  tspkfslgar teknhfessp lptspkflrp ncvyaseglp gkgpgaqekc klenhtspdv
841  hmlpgggahg strdqsi
```

Mouse Kv2.1 C1a Peptide (SEQ ID NO: 6)

NFSEFYKEQKRQEKAIKRREALERAKRNGSIVSMNMKDAFARSIEMMDIV
VEKNGEGVAKKDKVQDNHLSPNKWKWTKRALSETSSSKSFETKEQGSPEK
ARSSSSPQHLNV

The C1a peptide of mouse Kv2.1 (SEQ ID NO: 6) corresponds to residues 415-526 of full-length mouse Kv2.1 (SEQ ID NO: 5).

Provided below are an alignment of the human (SEQ ID NO: 2), rat (SEQ ID NO: 4) and mouse (SEQ ID NO: 6) C1a peptide sequences, and a consensus sequences of human, rat and mouse C1a peptides.

Alignment of Kv2.1 C1a Peptide Sequences:

```
Human  NFSEFYKEQKRQEKAIKRREALERAKRNGSIVSMNMEDAFARSIEMMDIVVEKNGENMGE
Rat    NFSEFYKEQKRQEKAIKRREALERAKRNGSIVSMNMEDAFARSIEMMDIVVEKNGESIAK
Mouse  NFSEFYKEQKRQEKAIKRREALERAKRNGSIVSMNMEDAFARSIEMMDIVVEKNGEGVAK
       ************************************************:.*

Human  KDKVQDNHLSPNEWKWTERTLSETSSSKSFETKEQGSPEKARSSSSPQHLNV    (SEQ ID NO: 2)
Rat    KDKVQDNHLSPNEWKWTKRALSETSSSKSFETKEQGSPEKARSSSSPQHLNV    (SEQ ID NO: 4)
Mouse  KDKVQDNHLSPNEWKWTKRALSETSSSKSFETKEQGSPEKARSSSSPQHLNV    (SEQ ID NO: 6)
       *****************:.********************************
```

Human, Rat and Mouse C1a Peptide Consensus Sequence:

(SEQ ID NO: 7)

NFSEFYKEQKRQEKAIKRREALERAKRNGSIVSMNMKDAFARSIEMMDIV
VEKNGEX$_1$X$_2$X$_3$KKDKVQDNHLSPNKWKWTKRX$_4$LSETSSSKSFETKEQGS
PEKARSSSSPQHLNV

X$_1$ = N, S or G

X$_2$ = M, I or V

X$_3$ = G or A

X$_4$ = T or A

Minimal Syntaxin Binding Sequence:
HLSPNKWKW (set forth herein as SEQ ID NO: 9; and corresponding to residues 478-486 of SEQ ID NO: 3, residues 482-490 of SEQ ID NO: 1 and residues 478-486 of SEQ ID NO: 5)

Provided are isolated Kv2.1 peptides capable of disrupting binding of Kv2.1 to syntaxin. In some embodiments, provided is an isolated Kv2.1 polypeptide 8 to 20 amino acids in length, wherein the amino acid sequence of the polypeptide comprises at least 8 consecutive amino acids of SEQ ID NO: 7. In other embodiments, the isolated Kv2.1 polypeptide is 10 to 15 amino acids in length and comprises at least 10 consecutive amino acids of SEQ ID NO: 7. In some examples, the Kv2.1 polypeptide comprises at least 8 or at least 10 consecutive amino acids of SEQ ID NO: 2, SEQ ID NO: 4, SEQ ID NO: 6 or SEQ ID NO: 9.

In some embodiments, the amino acid sequence of the Kv2.1 polypeptide comprises at least 8 consecutive amino acids of residues 62-112 of SEQ ID NO: 7. In other embodiments, the amino acid sequence of the Kv2.1 polypeptide comprises at least 10 consecutive amino acids of residues 62-112 of SEQ ID NO: 7. In particular examples, the Kv2.1 polypeptide comprises at least 8 or at least 10 consecutive amino acids of residues 62-112 of SEQ ID NO: 2, SEQ ID NO: 4 or SEQ ID NO: 6.

In some embodiments, provided is an isolated or recombinant polypeptide comprising at least 8 consecutive amino acids of SEQ ID NO: 9, wherein the polypeptide is no more than 20 amino acids in length and shares at least 90% sequence identity with the Kv2.1 polypeptide sequence of SEQ ID NO: 7. In some examples, the polypeptide is 10 to 15 amino acids in length. In some examples, the polypeptide shares at least 90% sequence identity with the Kv2.1 polypeptide sequence of SEQ ID NO: 2, SEQ ID NO: 4 or SEQ ID NO: 6. In particular examples, the polypeptide shares at least 95% sequence identity with the Kv2.1 polypeptide sequence of SEQ ID NO: 2, SEQ ID NO: 4 or SEQ ID NO: 6. In specific non-limiting examples, the polypeptide comprises or consists of the amino acid sequence of SEQ ID NO: 9.

Also contemplated are variants of the Kv2.1 peptides, such as variants exhibiting increased stability and/or increased affinity for syntaxin. Thus, in some embodiments, provided are Kv2.1 polypeptides comprising an amino acid sequence at least 85%, at least 90%, at least 95%, at least 96%, at least 97%, at least 98% or at least 99% identical to SEQ ID NO: 2, SEQ ID NO: 4, SEQ ID NO: 6, SEQ ID NO: 7, or SEQ ID NO: 9, or a portion thereof (such as a portion about 8 to about 20 amino acids in length). In other embodiments, provided are Kv2.1 polypeptides comprising no more than 5, no more than 4, no more than 3, no more than 2 or no more than 1 conservative amino acid substitution(s).

V. Administration of Kv2.1 Peptides

Methods of administering therapeutic proteins and peptides are well known in the art. In some embodiments of the disclosed methods, Kv2.1 peptides and fusion proteins are administered to a subject for the treatment of cerebral ischemia, stroke (such as ischemic stroke or hemorrhagic stroke), CNS trauma/injury, traumatic brain injury, a neurodegenerative disease, or any other condition associated with neuronal damage and/or neuronal cell death. When administering Kv2.1 peptides (or fusion proteins thereof), one must consider the appropriate target site based on the disease to be treated. If the site of action is the central nervous system, the protein must be able to cross the blood brain barrier (BBB) or be delivered directly to the target site in the brain.

Methods of administering neurotrophic factors for the treatment of a variety of neurodegenerative diseases has been previously described (see, for example, Levy et al., *Biodrugs* 19(2):97-127, 2005; Gill et al., *Nat Med* 9:589-595, 2003; Nutt et al., *Neurology* 60:69-73, 2003; Olson et al., *J Neural Transm Park Dis Dement Sect* 4:79-95, 1992; Eriksdotter et al., *Dement Geriatr Cogn Disord* 9:246-257, 1998; Bradley, *Ann Neurol* 38:971, 1995; The BDNF Study Group Phase III, *Neurology* 52:1427-1433, 1999; Ochs et al., *Amyotroph Lateral Scler Other Motor Neuron Disord* 1:201-206, 2000; ALS CNTF Treatment Study Group, *Neurology* 46(5):1244-1249, 1996; Miller et al., *Neurology* 47:1329-1331, 1996; Miller et al., *Ann Neurol* 39:256-260, 1996; Lai et al., *Neurology* 49:1621-1630, 1997; Borasio et al., *Neurology* 51:583-586, 1998).

In some embodiments, the Kv2.1 peptide or fusion protein is administered by direct infusion into the brain, such as by intracerebroventricular (ICV) injection/infusion, intrastriatal injection, intranigral injection, intracerebral injection, infusion into the putamen, intrathecal infusion (such as by using an implanted pump) or by subcutaneous injection. Intranasal administration of peptides also leads to delivery to the CNS. Thus, in some examples, the Kv2.1 peptide or fusion protein is administered intranasally In some embodiments, Kv2.1 peptides or fusion proteins are administered using biodegradable microparticles (~1-100 µm) or nanoparticles (~50-1000 nm). Nanoparticles and microparticles (also known as nanospheres or microspheres) are drug delivery vehicles that can carry encapsulated drugs such as synthetic small molecules, proteins, peptides, cells and nucleic acid based biotherapeutics for either rapid or controlled release. A variety of molecules (e.g., proteins, peptides and nucleic acid molecules) can be efficiently encapsulated in nano/microparticles using processes well known in the art.

The nano/microparticles for use with the methods described herein can be any type of biocompatible particle, such as biodegradable particles, such as polymeric particles, including, but not limited to polyamide, polycarbonate, polyalkene, polyvinyl ethers, and cellulose ether nano/microparticles. In some embodiments, the particles are made of biocompatible and biodegradable materials. In some embodiments, the particles include, but are not limited to particles comprising poly(lactic acid) or poly(glycolic acid), or both poly(lactic acid) and poly(glycolic acid). In particular embodiments, the particles are poly(D,L-lactic-co-glycolic acid) (PLGA) particles.

Other biodegradable polymeric materials are contemplated for use with the methods described herein, such as poly(lactic acid) (PLA) and polyglycolide (PGA). Additional useful nano/microparticles include biodegradable poly(alkylcyanoacrylate) particles (Vauthier et al., *Adv. Drug Del. Rev.* 55: 519-48, 2003).

Various types of biodegradable and biocompatible nano/microparticles, methods of making such particles, including PLGA particles, and methods of encapsulating a variety of synthetic compounds, proteins and nucleic acids, has been well described in the art (see, for example, U.S. Publication No. 2007/0148074; U.S. Publication No. 20070092575; U.S. Patent Publication No. 2006/0246139; U.S. Pat. No. 5,753,234; U.S. Pat. No. 7,081,489; and PCT Publication No. WO/2006/052285). In addition, microsphere-mediated delivery of proteins to the central and peripheral nervous system has been described in, for example, US Patent Application Publication No. 2011/0217264.

The following examples are provided to illustrate certain particular features and/or embodiments. These examples should not be construed to limit the disclosure to the particular features or embodiments described.

EXAMPLES

Example 1: Methods

This example describes the materials and methods used for the studies described in Example 2.

Cell Culture and Transfection Procedures

For electrophysiological experiments, mixed cortical neuronal/glial cultures were prepared from embryonic day 16 (E16) Sprague-Dawley rats (Charles River Laboratories, Wilmington, Mass., USA). Donor rats were euthanized by gradual $CO_2$ exposure. Cortices were dissociated with trypsin, and the resultant cell suspension, adjusted to 670,000 cells per well, was plated on glass coverslips in 6-well plates as described previously (Hartnett et al., *J Neurochem* 68, 1836-1845, 1997). Non-neuronal cell proliferation was inhibited after two weeks in culture with 1-2 µM cytosine arabinoside, and cultures utilized at three to four weeks in vitro. For neuronal transfection, cells were treated for five hours in serum-free medium with 2 µL LIPOFECTAMINE™ 2000 (Invitrogen, Carlsbad, Calif.), 50 µL Optimem (GIBCO, Grand Island, N.Y.), and 1.5 µg DNA per well. For CHO cell transfections, cells were plated on coverslips in 24-well plates at a density of $5.6 \times 10^4$ cells per well for electrophysiological measurements or in 100 mm dishes at a density of $1.7 \times 10^6$ cells per dish for biochemical studies. Cells were treated for 3-4 hours in serum-free medium with a total of 1.2 µL LIPOFECTAMINE™ and 0.28 µg DNA per well for electrophysiology, or 55.1 µL LIPOFECTAMINE™ and 7.33 µg DNA per dish for biochemistry. Following transfection, cells were maintained in F12 medium containing fetal bovine serum at 37° C., 5% $CO_2$ for 24 hours prior to experimentation.

Drug Treatments and Antibodies

The apoptotic stimulus for electrophysiological experiments was 10 minute exposure to 30 µM 2,2'-dithiodipyridine (DTDP) at 37° C., 5% $CO_2$. The DTDP-containing solution was removed prior to three-hour incubation in fresh medium containing 10 µM butoxy-carbonyl-aspartate-fluoromethyl ketone (BAF), a cysteine protease inhibitor that maintains cell viability without affecting $K^+$ currents. Antibodies were purchased from the following suppliers: rabbit anti-syntaxin from Abcam (Cambridge, Mass.); mouse anti-syntaxin from Millipore (Temecula, Calif.); mouse anti-Kv2.1 from NeuroMab (Davis, Calif.).

Electrophysiological Measurements

Current recordings were performed on eGFP-positive co-transfected neurons or CHO cells using the whole-cell patch clamp configuration technique as described previously (McLaughlin et al., *J Neurosci* 21, 3303-3311, 2001). The intracellular (electrode) solution contained (in mM): 100 K-gluconate, 11 EGTA, 10 KCl, 1 $MgCl_2$, 1 $CaCl_2 \times 2H_2O$, 10 HEPES; pH adjusted to 7.2 with concentrated KOH; 2.2 ATP and 0.33 GTP were added and the osmolarity was adjusted to 280 mOsm with sucrose. The extracellular solution contained (in mM): 115 NaCl, 2.5 KCl, 2.0 $MgCl_2$, 10 HEPES, 10 D-glucose; 0.25 µM tetrodotoxin; pH adjusted to 7.2. Measurements were obtained under whole-cell voltage clamp with an Axopatch-1D amplifier and pClamp software (Molecular Devices, Sunnyvale, Calif.), using 2-3 MΩ recording electrodes. Electrodes were pulled from 1.5 mm borosilicate glass (Warner Instruments, Hamden, Conn.) with a model P-97 mechanical pipette puller (Sutter Instruments, Novato, Calif.). Series resistance was partially compensated (80%) in all cases. Currents were filtered at 2 kHz and digitized at 10 kHz with a Digidata 1440A Digitizer (Molecular Devices). $K^+$ currents were evoked with incremental 10 mV voltage steps to +80 mV from a holding potential of −80 mV. To determine current density values, steady-state current amplitudes were measured 180 msec after the initiation of the +10 mV step and normalized to cell capacitance. For current clamp experiments, the intracellular (electrode) solution contained (in mM): 94 K-gluconate, 30 KCl, 10 phosphocreatine di-tris salt, 10 HEPES, 0.2 EGTA, 4 ATP, 0.3 GTP; pH adjusted to 7.3 with concentrated KOH. The extracellular solution contained (in mM): 146 NaCl, 7.8 glucose, 20 HEPES, 4.7 KCl, 0.6 $MgSO_4$, 1.6 $NaHCO_3$, 0.13 $NaH_2PO_4$, 2.5 $CaCl_2$; pH adjusted to 7.3 with concentrated KOH. Measurements were performed at room temperature with an Axoclamp 2B amplifier and G-clamp 2.2 software (Kullmann et al., *J Neurophysiol* 91, 542-54, 2004). Voltage responses were induced with 1 s current steps ranging from −120 pA to 120 pA. Virtual excitatory synapses were implemented under dynamic clamp according to $g_{syn}(t)=k*t*\exp(-t/\tau)$ with tau=1.5 ms and Erev=0 mV. By repeatedly adjusting the scaling factor k, an automated binary search algorithm determined threshold synaptic conductance (thresh-$g_{syn}$), the conductance required to reach firing threshold (Kullmann et al., *J Neurophysiol* 91, 542-54, 2004).

Immunoprecipitation

Protein was harvested by washing cell culture dishes with ice cold PBS followed by a short incubation with 1% 3-[(3-cholamidopropyl) dimethylammonio]-1-propanesulfonate buffer. Protein A/G agarose bead slurry (Santa Cruz, Dallas, Tex.) was added to the samples and rocked at 4° C. for 1 hour in order to pre-clear non-specific protein binding. Samples were then incubated overnight at 4° C. with the appropriate immunoprecipitating antibodies. Following another incubation with the bead slurry, the protein samples were prepared/denatured by the addition of sample preparation buffer (625 mM Tris, 25% glycerol, 2% sodium dodecyl sulfate (SDS), 0.01% bromophenol blue and 5% β-mercaptoethanol) and heated at 95° C. for 5 min prior to SDS polyacrylamide gel electrophoresis and immunoblotting.

Electrophoresis and Immunoblotting

Protein samples from equal amounts of cell lysate were separated on 10% sodium dodecyl sulfate SDS polyacrylamide gels by electrophoresis using the Mini Protean 3 System (Bio-Rad, Hercules, Calif.). Separated protein bands were transferred onto 0.2 µm nitrocellulose membranes (Bio-Rad), blocked with 1% bovine serum albumin (BSA) in PBS with 0.05% Tween 20 (PBST) at room temperature for 1 hour, and probed with appropriate primary antibodies diluted in PBST. Blots were then incubated with infrared fluorescent goat secondary antibodies at room temperature for 1 hour, visualized using the Odyssey Imaging System (LI-COR Biosciences, Lincoln, Nebr.), and quantified using infrared fluorimetry.

Viability Assays

Viability of transfected neurons was assessed by cell counts of GFP+ cells. Twenty-four hours after transfection with eGFP together with either an empty vector or a plasmid expressing $C1a_{441-522}$, cultures were treated overnight with either vehicle or microglia (50,000 cells/mL) (Cheepsunthorn et al., *Glia* 35, 53-62, 2001) plated directly on top of neurons and activated by interferon-γ (IFN-γ) and lipopolysaccharide (UPS) (Knock et al., *Glia* 56, 89-96, 2008). The following clay, cells were preserved using 4% paraformaldehyde as reported previously (Aras et al., *Curr Protoc Neurosci* Chapter 7: Unit 7 18, 2008). GFP+ cells were counted in 20 random areas per coverslip using a 20× objective. Coverslips were chosen at random by the person performing the cell counts. Experiments were performed in three separate culture dates, with three coverslips per condition, per experiment. Results are expressed a percent of control, vehicle-exposed sister cultures.

Example 2: Syntaxin-Binding Domain of Kv2.1 is Essential for the Expression of Apoptotic $K^+$ Currents The SNARE protein syntaxin has been shown to interact with the most proximal region of the Kv2.1 C-terminus, termed C1a, in a process regulating dense-core vesicle-mediated exocytosis in PC12 cells and dorsal root ganglion (DRG) neurons (Singer-Lahat et al., *J Neurosci* 27, 1651-1658, 2007; Singer-Lahat et al., *PLoS One* 3, e1381, 2008; Feinshreiber et al., *J Cell Sci* 123, 1940-1947, 2010). Introduction of an isolated Kv2.1-derived C1a peptide disrupted Kv2.1/syntaxin binding and inhibited the physiological consequences of this interaction (Singer-Lahat et al., *J Neurosci* 27, 1651-1658, 2007). In addition, the association between Kv2.1 and syntaxin is enhanced under conditions that lead to apoptosis (McCord and Aizenman, *Proc Natl Acad Sci USA* 110, 13988-13993, 2013), suggesting that interfering with this interaction may provide a novel neuroprotective therapeutic strategy. The following studies evaluate (1) whether the syntaxin-binding domain of Kv2.1 is necessary for the apoptotic $K^+$ current enhancement, and (2) if introduction of C1a or sub-domains of the peptide can prevent the increase in $K^+$ currents and be neuroprotective in vitro.

Syntaxin-Interacting Domain of Kv2.1 is Required for Apoptotic $K^+$ Current Enhancement The most proximal 110 amino acids of the C-terminus of Kv2.1, corresponding to amino acids 411-522 of the rat protein sequence (SEQ ID NO: 4), contain the channel's syntaxin binding site (C1a; Tsuk et al., *Mol Pharmacol* 67, 480-488, 2005). Previous studies in DRG neurons and *Xenopus* oocytes demonstrated that overexpression of a Kv2.1 channel mutant lacking its C1a domain (Kv2.1ΔC1a) results in a marked reduction of co-immunoprecipitation between syntaxin and Kv2.1, as well as an inhibition of Kv2.1-mediated exocytosis (Singer-Lahat et al., *J Neurosci* 27, 1651-1658, 2007; Feinshreiber et al., *J Cell Sci* 123, 1940-1947, 2010). As syntaxin is also involved in the apoptotic regulation of Kv2.1-mediated $K^+$ currents (Pal et al., *Cell Death Differ* 13, 661-667, 2006), it was investigated whether the C1a region of Kv2.1 was required for this process. To explore this possibility, CHO cells, a recombinant expression system that lacks endogenous voltage-gated $K^+$ channels (Yu and Kerchner, *J Neurosci Res* 52, 612-617, 1998), yet has all the cell signaling components required to produce an apoptotic current enhancement in Kv2.1-transfected cells (Pal et al., *J Neurosci* 23, 4798-4802, 2003), were used. CHO cells expressing either wild-type (WT) Kv2.1, Kv2.1ΔC1a, or a 1:1 ratio of Kv2.1 and Kv2.1ΔC1a were subjected to a 10-minute exposure of 30 µM 2,2'-dithiodipyridine (DTDP), a thiol oxidant that initiates a $Zn^{2+}$- and $Ca^{2+}$-dependent signaling cascade responsible for the enhancement of Kv2.1 $K^+$ currents observed during apoptosis (McLaughlin et al., *J Neurosci* 21, 3303-3311, 2001; McCord and Aizenman, *Proc Natl Acad Sci USA* 110, 13988-13993, 2013). DTDP treatment was followed by 3-hour maintenance in butoxy-carbonyl-aspartate-fluoromethyl ketone (BAF; 10 µM), a broad-spectrum protease inhibitor used during recording for its ability to prevent apoptosis downstream of the $K^+$ current enhancement (McLaughlin et al., *J Neurosci* 21, 3303-3311, 2001).

Figure 1B:
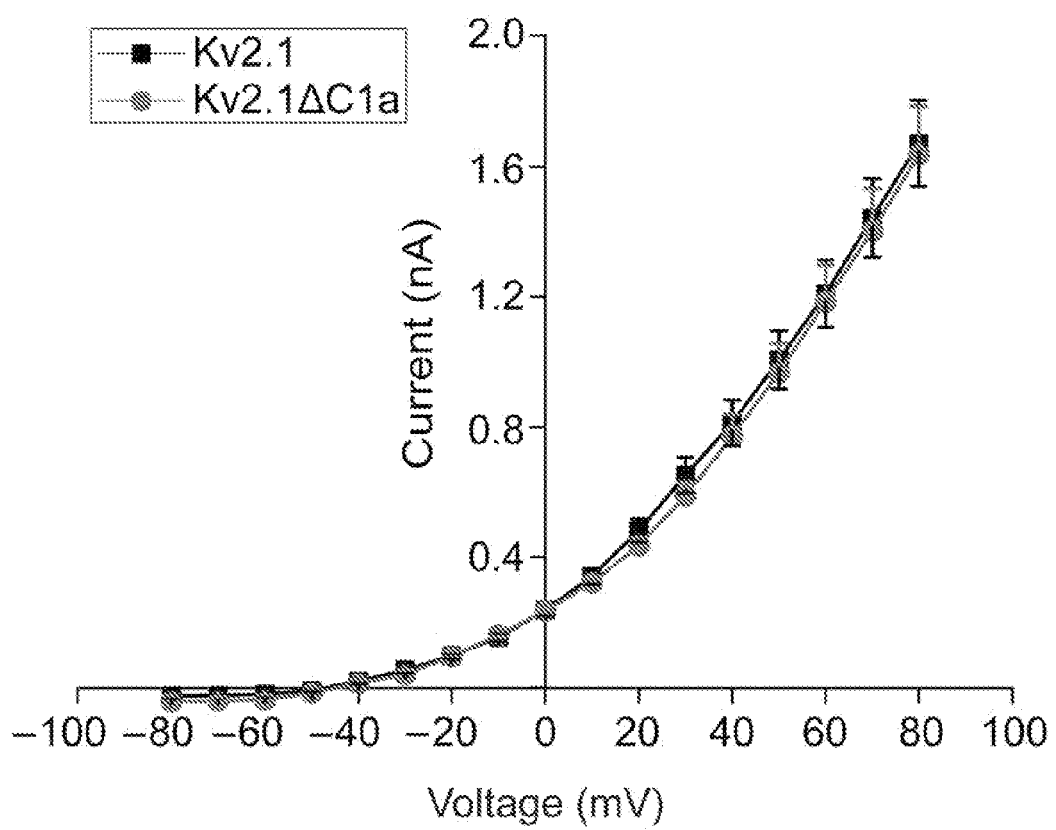

The DTDP-induced increase in $K^+$ currents observed in Kv2.1-expressing CHO cells was absent in cells expressing Kv2.1ΔC1a, suggesting that syntaxin binding to Kv2.1 is an integral component of the machinery mediating insertion of new channels into the plasma membrane during oxidative injury. Further, cells transfected with a 1:1 ratio of Kv2.1 and Kv2.1ΔC1a plasmids were also refractory to the actions of DTDP, demonstrating that even when WT Kv2.1 is present, expression of the mutant channel is sufficient to block the effect of the oxidant on the apoptotic increase in Kv2.1-mediated $K^+$ currents (FIG. 1A). Cells expressing the mutant channel exhibited $K^+$ currents that appeared indistinguishable from WT Kv2.1-mediated currents (FIG. 1B), indicating that normal trafficking and expression of this channel is not dependent on the cytoplasmic C1a region, as shown previously (Singer-Lahat et al., *J Neurosci* 27, 1651-1658, 2007).

Figure 2A:
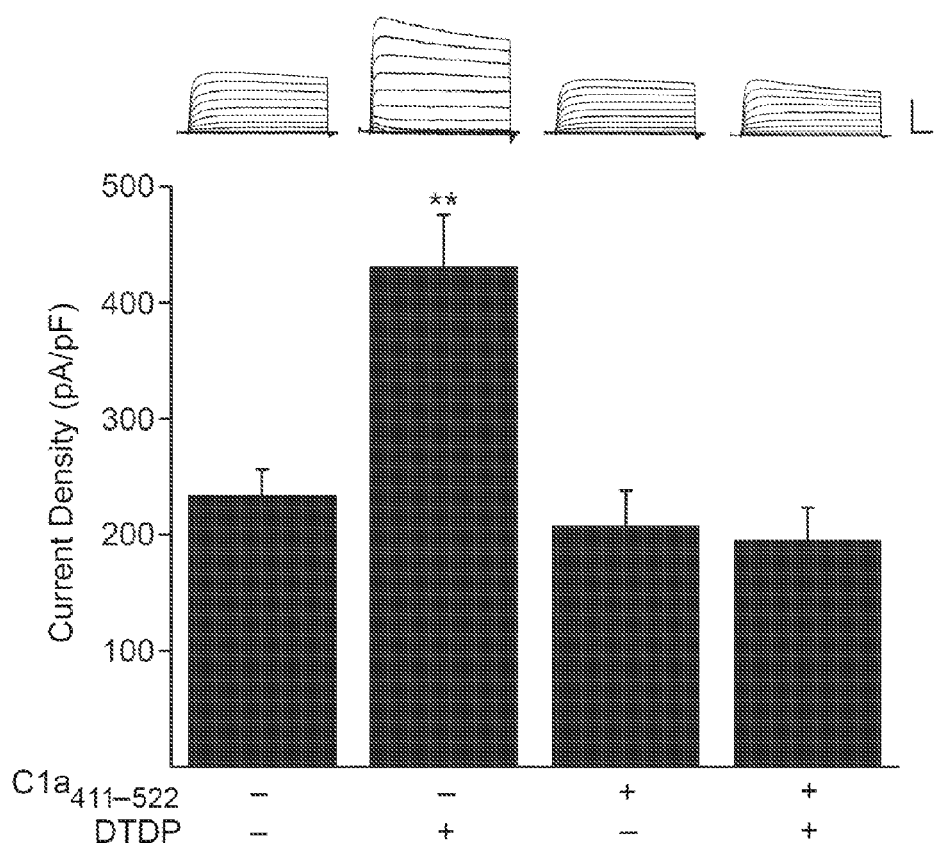
FIGS. 2A-2B: C1a expression blocks the increase in oxidant-induced $K^+$ currents normally observed following DTDP exposure.
Figure 2B:
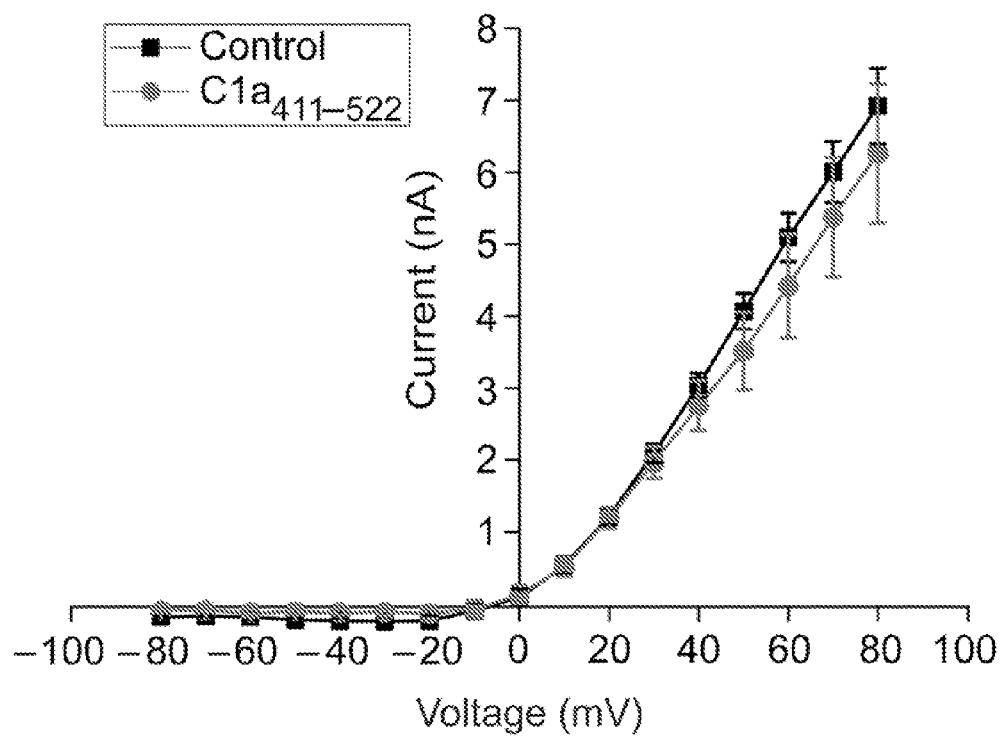

Kv2.1-Derived Syntaxin-Binding Peptide Blocks Oxidant-Induced Increase in $K^+$ Currents Incubation with a Kv2.1-derived GST-fusion C1a peptide prevents the binding of syntaxin to endogenous Kv2.1 in PC12 cells (Singer-Lahat et al., *PLoS One* 3, e1381, 2008). Thus, it was investigated whether expression of C1a in cortical neurons was sufficient to prevent the increase in Kv2.1 $K^+$ currents triggered by exposure to an oxidative insult. Unlike cells expressing an empty vector, those transfected with a C1a-expressing plasmid failed to exhibit the enhanced $K^+$ current densities normally elicited by DTDP (FIG. 2A). Notably, C1a had no effect on non-apoptotic, basal delayed-rectifier $K^+$ currents (FIG. 2B), again suggesting that the interaction of syntaxin with the C1a region of native Kv2.1 channels is important for their apoptotic regulation, but may not be critical for their steady state expression.

Refining the Syntaxin-Interacting Region within C1a

After establishing that C1a effectively precluded the oxidant-induced $K^+$ current increase in neurons, studies were performed to identify the sub-domains within C1a that could retain the ability to disrupt Kv2.1/syntaxin binding. C1a was divided into overlapping proximal and distal segments, hereafter referred to as $C1a_{411-472}$ and $C1a_{441-522}$, respectively. Co-immunoprecipitation experiments were performed to compare the ability of C1a and the smaller segments to displace Kv2.1 from syntaxin. Syntaxin immunoprecipitates of protein samples obtained from CHO cells transfected with a syntaxin-expressing plasmid, and co-transfected with Kv2.1 together with C1a, $C1a_{411-472}$, or $C1a_{441-522}$, were probed for Kv2.1. Both C1a and the distal segment, $C1a_{441-522}$, inhibited Kv2.1/syntaxin binding, while the proximal segment, $C1a_{411-472}$, did not (FIG. 3A). These results reveal that syntaxin binds to Kv2.1 in the more distal portion of the C1a domain of the channel's C-terminus. In subsequent experiments, it was found that similar to $C1a_{411-472}$, the overlapping middle segment, $C1a_{441-472}$, had no effect on syntaxin's ability to bind to Kv2.1 (mean±SEM ratio of Kv2.1 to syntaxin immunoblots: baseline=0.24±0.08, $C1a_{441-472}$=0.25±0.1; n=3), suggesting that the syntaxin binding site on Kv2.1 is most likely found within residues 472-522 of C1a.

Figure 3B:
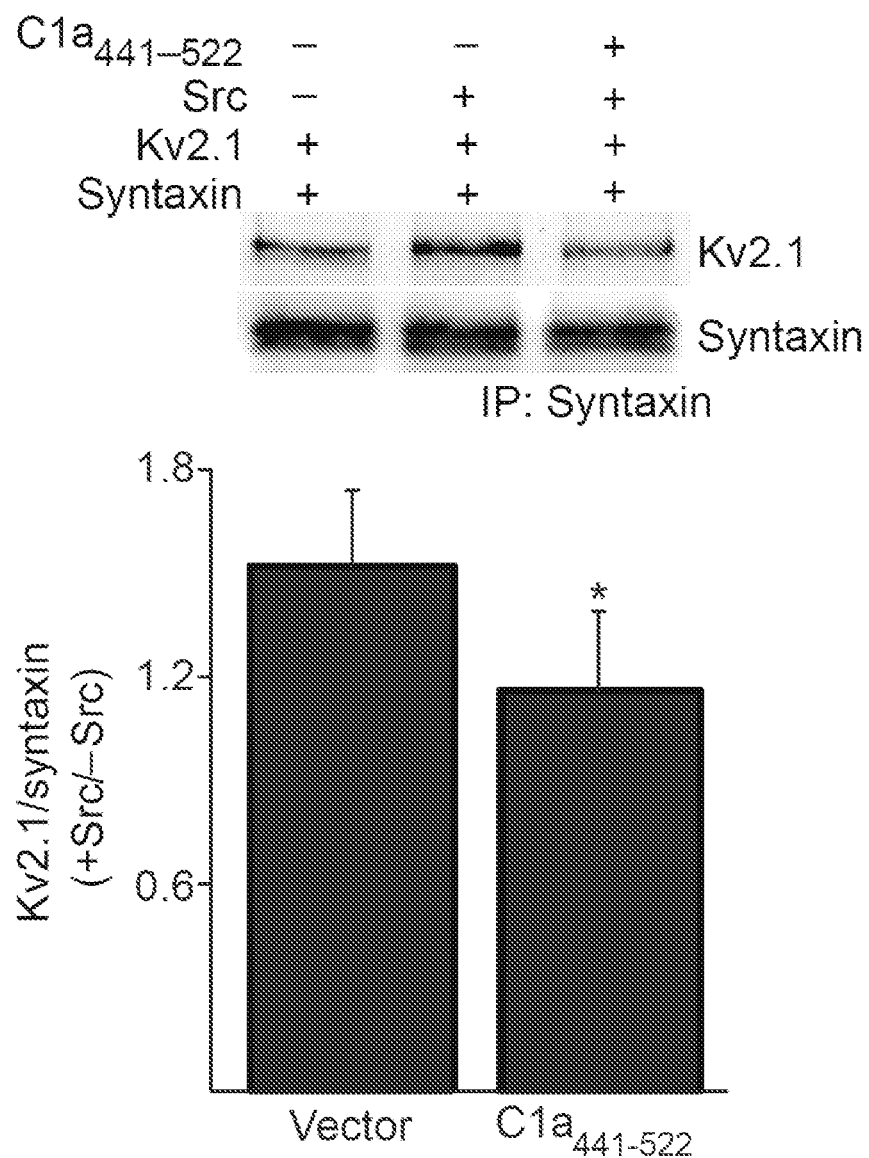

It was previously shown that in CHO cells, overexpression of Src kinase, which induces phosphorylation of two Kv2.1 residues required for apoptosis, enhances the binding of Kv2.1 to syntaxin (McCord and Aizenman, *Proc Natl Acad Sci USA* 110, 13988-13993, 2013). Therefore, it was evaluated whether $C1a_{441-522}$ also retained the ability to displace Kv2.1 from syntaxin under these conditions, which was indeed the case (FIG. 3B).

Figure 4:
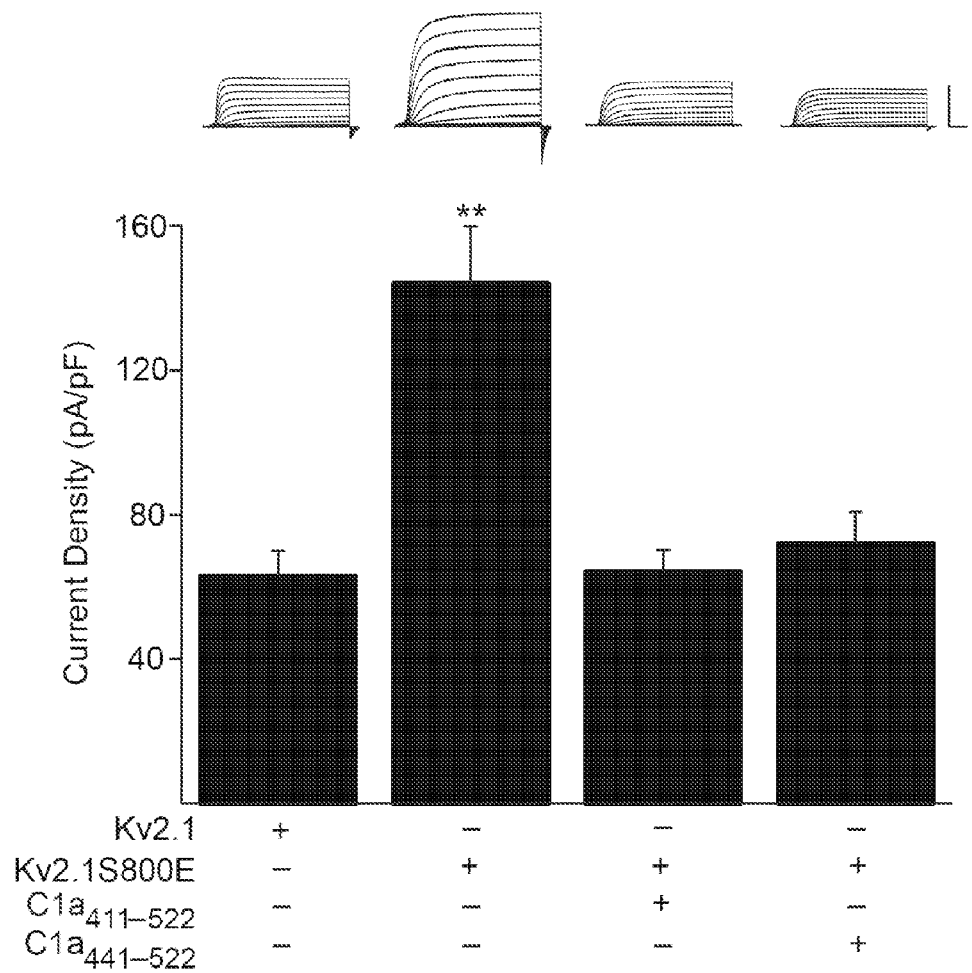
FIG. 4: C1a and $C1a_{441-522}$ block K⁺ current enhancement in CHO cells. Representative whole-cell K⁺ currents and pooled mean±SEM current densities recorded from CHO cells expressing Kv2.1 (n=14), Kv2.1S800E (n=11), Kv2.1S800E+C1a (n=16) or Kv2.1S800E+$C1a_{441-522}$ (n=14). Currents were evoked by a series voltage steps from −80 mV to +80 mV in 10 mV increments. To determine current density values, steady-state current amplitudes were measured 180 msec after the initiation of the +10 mV step and normalized to cell capacitance. Scale bars: 5 nA, 25 msec; **p<0.01, ANOVA/Dunnett.

$C1a_{441-522}$ Blocks $K^+$ Current Enhancement in CHO Cells and is Neuroprotective Once it was established that both C1a and $C1a_{441-522}$ were able to disrupt binding of syntaxin to Kv2.1, it was evaluated whether expression of C1a and $C1a_{441-522}$ was also able to prevent the apoptotic $K^+$ current enhancement. CHO cells expressing a pseudo-phosphorylated Kv2.1 channel mutant, Kv2.1S800E, which exhibits an innate, phosphorylation-independent increase in $K^+$ current densities that mimics the enhanced currents observed in apoptogen-exposed, WT Kv2.1-expressing cells (Redman et al., *Proc Natl Acad Sci USA* 104, 3568-3573, 2007) were used to investigate this. CHO cells were transfected with WT Kv2.1 or Kv2.1S800E in the absence or presence of either C1a or $C1a_{441-522}$. Similar to what was observed in DTDP-treated, C1a-expressing neurons, co-transfection with C1a suppressed the enhanced $K^+$ currents normally observed in Kv2.1S800E-expressing CHO cells. $C1a_{441-522}$ also blocked the increase in currents produced by the S800E channel mutant (FIG. 4), further indicating that syntaxin binds to Kv2.1 within the most distal region of C1a.

Figure 5:
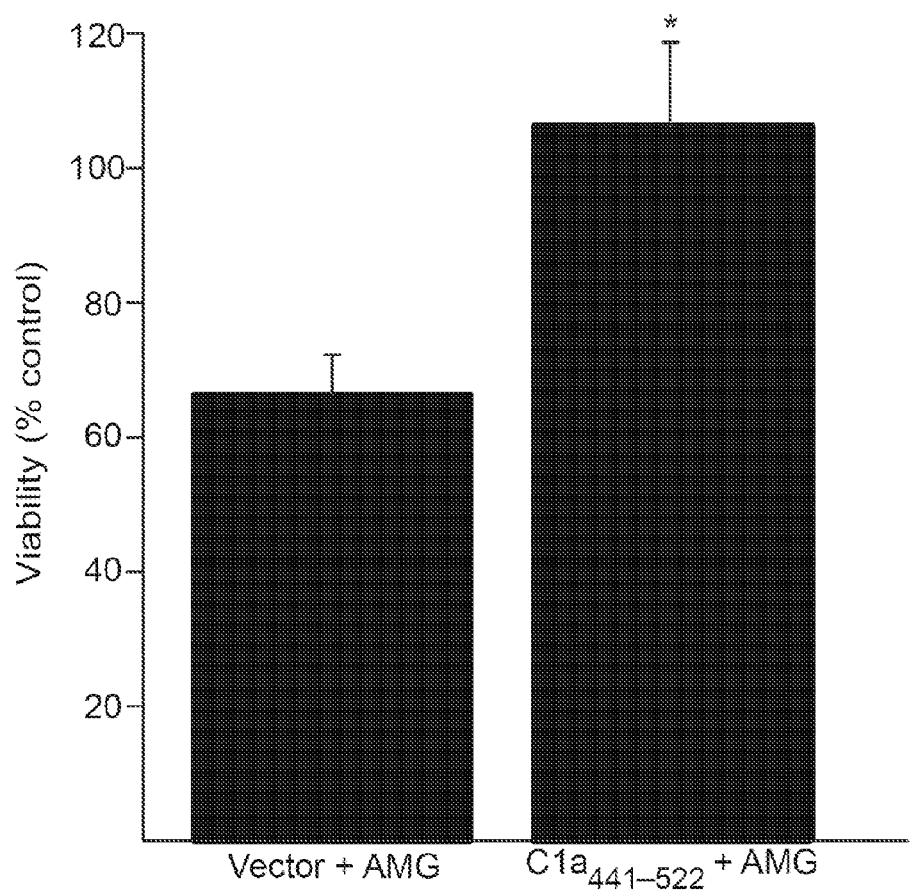
FIG. 5: $C1a_{441-522}$ protects against apoptotic cell death in cortical neurons. Cortical neurons were transfected with a GFP-expressing plasmid plus either an empty vector or a vector expressing $C1a_{441-522}$. Neuronal cell counts of GFP positive cells reveal that unlike vector-expressing neurons, those expressing $C1a_{441-522}$ are resistant to overnight exposure to activated microglia, a known inducer of Kv2.1-dependent neuronal cell death (Knoch et al., *Glia* 56, 89-96, 2008). Mean±SEM survival (expressed as a percent of control, vehicle-exposed, sister cultures) of GFP+ cells from three independent experiments; *p<0.05, t-test.
Figure 6A:
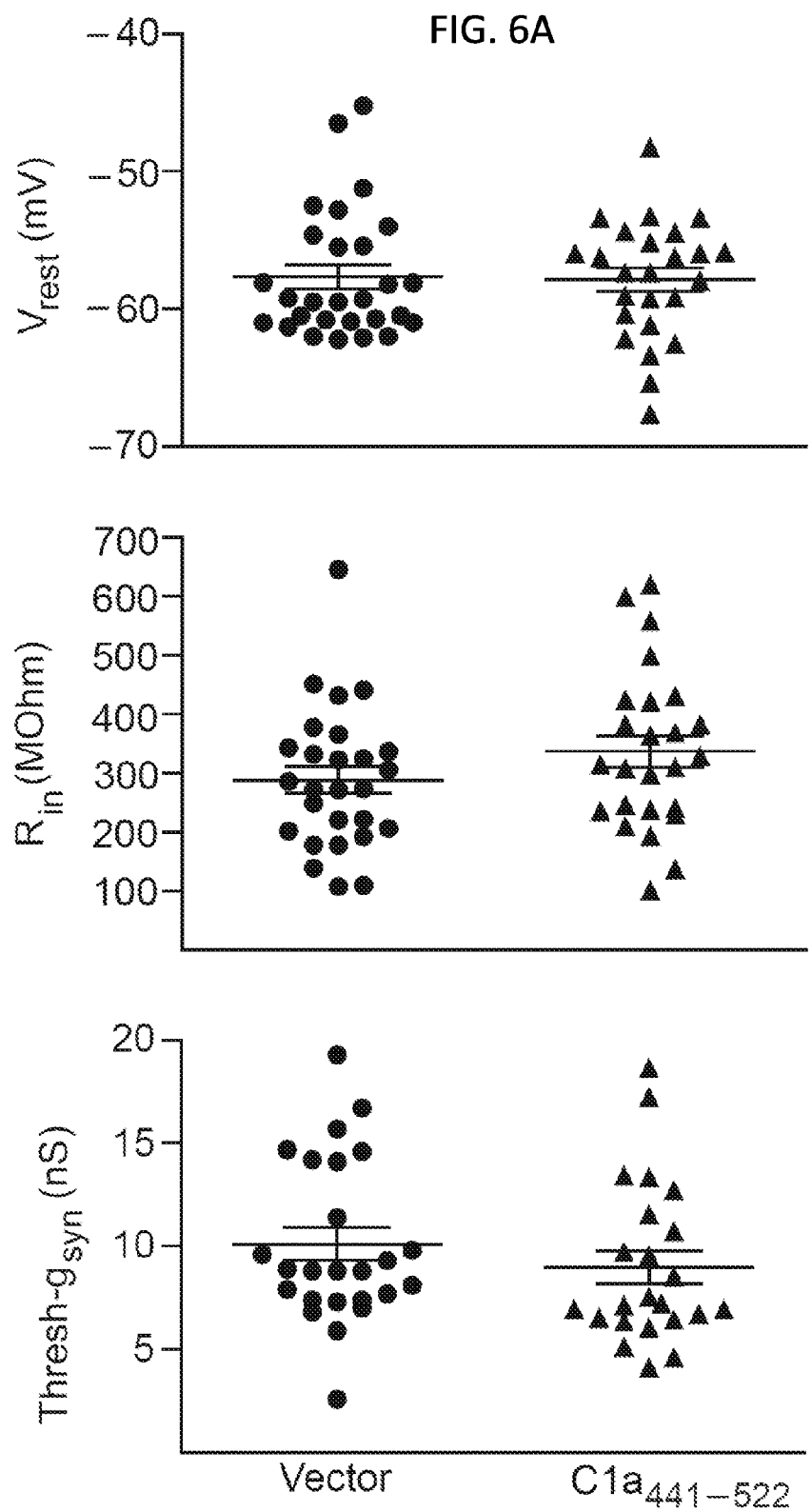
FIGS. 6A-6B: $C1a_{441-522}$ has minimal effect on electrical properties of neurons.
Figure 6B:
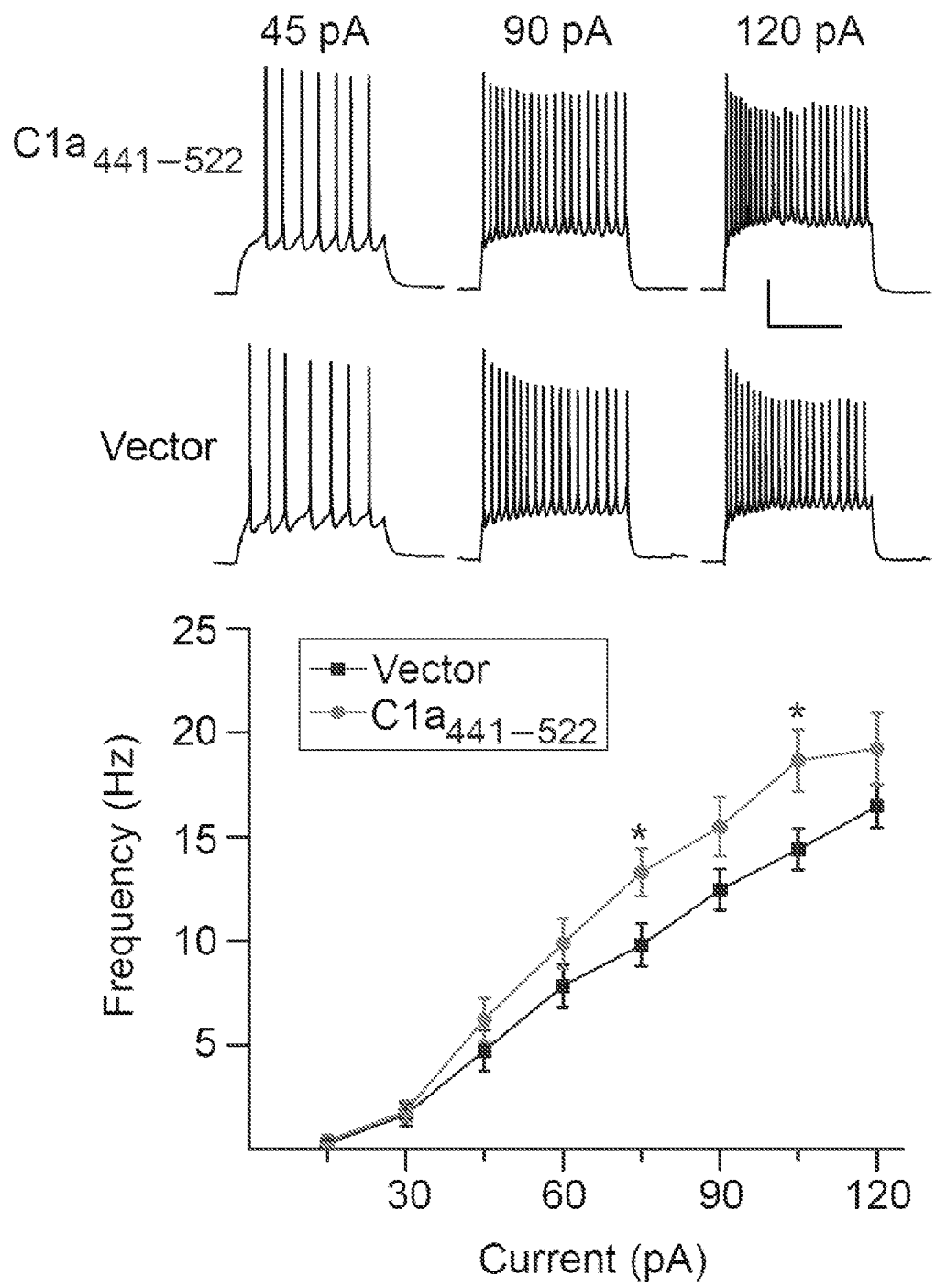

It was next evaluated whether C1a$_{441-522}$ was sufficient to protect neurons against oxidative injury. Cells expressing C1a$_{441-522}$ or an empty vector were exposed to activated microglia, a known inducer of Kv2.1-dependent neuronal cell death via peroxynitrite production and intraneuronal Zn$^{2+}$ liberation (Knoch et al., *Glia* 56, 89-96, 2008). While microglia reduced viability of vector-expressing cells by nearly 40%, there was no detrimental effect on neurons expressing C1a$_{441-522}$ (FIG. 5). Finally, a series of current-clamp experiments determined that vector- and C1a$_{441-522}$-expressing neurons showed no differences in resting membrane potential, input resistance, or threshold synaptic conductance (FIG. 6A). However, a small but significant increase in firing frequency as a function of depolarizing current in C1a$_{441-522}$-expressing neurons was observed, suggesting that C1a$_{441-522}$ may have a small effect on a neuron's propensity for firing action potentials (FIG. 6B). Overall, however, the expression of C1a$_{441-522}$ was relatively innocuous to neurons. Taken together, these findings suggest that targeting the interaction between Kv2.1 and syntaxin offers a novel therapeutic strategy in the prevention of neurodegeneration that does not substantially affect neuronal electrophysiological properties.

Figure 8:
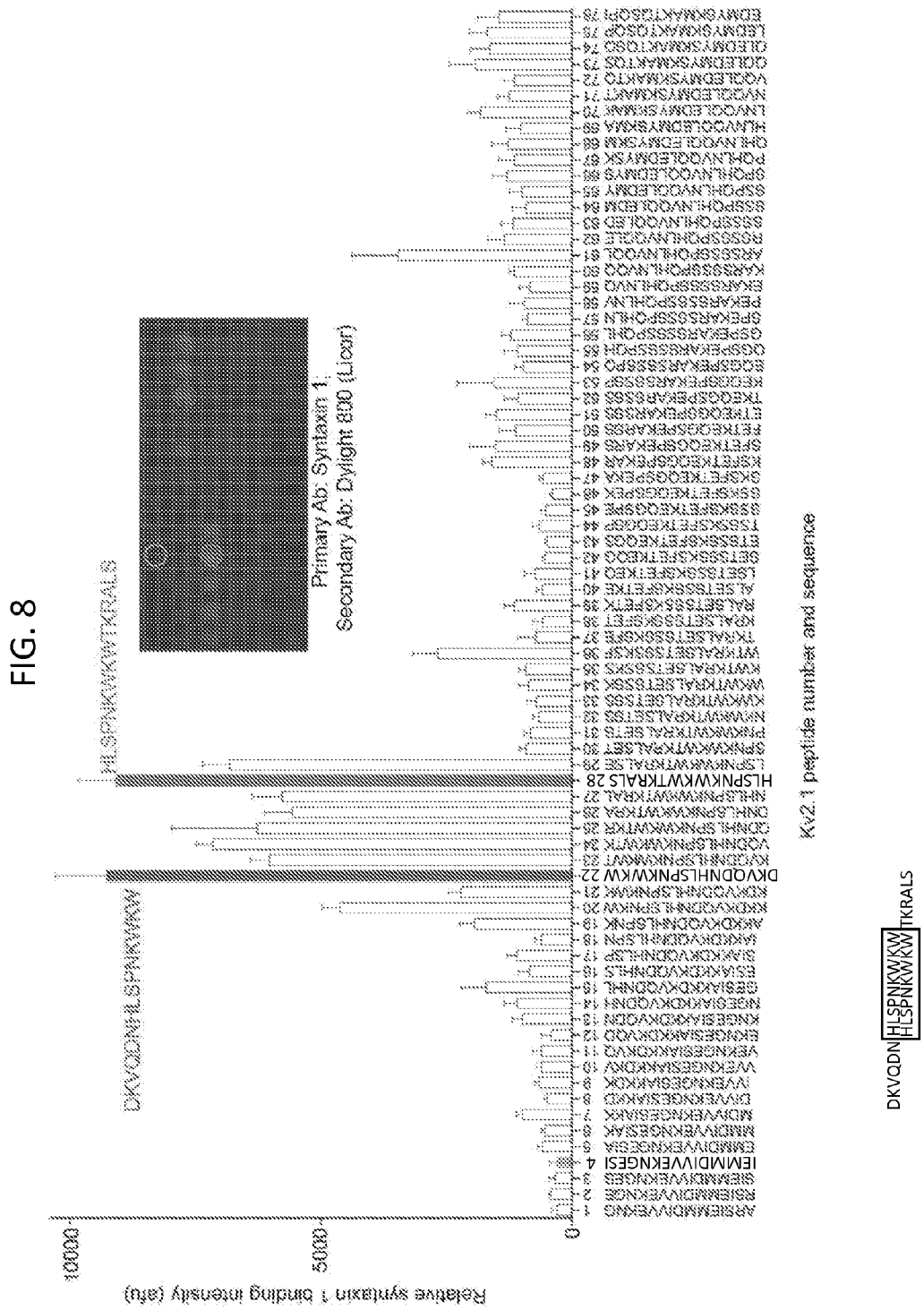
FIG. 8: Binding of Kv2.1 peptides to syntaxin. The 76 overlapping Kv2.1 peptides were spot-plated as an array onto a polyvinylidene fluoride membrane using the SPOTS-synthesis method. Membranes were incubated with a human syntaxin over-expressing CHO cell lysate and a far-Western analysis of syntaxin binding to the peptide arrays was performed using a commercially available syntaxin antibody and fluorescently tagged secondary antibody. Fluorescence intensity was quantified as an index of syntaxin binding to the spot array. Bars represent the mean+/−SEM of binding in four independent arrays. All 76 peptides are derived from rat Kv2.1 set forth as SEQ ID NO: 3 as follows: peptide number 1, residues 451-465 of SEQ ID NO: 3; peptide number 2, residues 452-466 of SEQ ID NO: 3; peptide number 3, residues 453-467 of SEQ ID NO: 3; peptide number 4, residues 454-468 of SEQ ID NO: 3; peptide number 5, residues 455-469 of SEQ ID NO: 3; peptide number 6, residues 456-470 of SEQ ID NO: 3; peptide number 7, residues 457-471 of SEQ ID NO: 3; peptide number 8, residues 458-472 of SEQ ID NO: 3; peptide number 9, residues 459-473 of SEQ ID NO: 3; peptide number 10, residues 460-474 of SEQ ID NO: 3; peptide number 11, residues 461-475 of SEQ ID NO: 3; peptide number 12, residues 462-476 of SEQ ID NO: 3; peptide number 13, residues 463-477 of SEQ ID NO: 3; peptide number 14, residues 464-478 of SEQ ID NO: 3; peptide number 15, residues 465-479 of SEQ ID NO: 3; peptide number 16, residues 466-480 of SEQ ID NO: 3; peptide number 17, residues 467-481 of SEQ ID NO: 3; peptide number 18, residues 468-482 of SEQ ID NO: 3; peptide number 19, residues 469-483 of SEQ ID NO: 3; peptide number 20, residues 470-484 of SEQ ID NO: 3; peptide number 21, residues 471-485 of SEQ ID NO: 3; peptide number 22, residues 472-486 of SEQ ID NO: 3; peptide number 23, residues 473-487 of SEQ ID NO: 3; peptide number 24, residues 474-488 of SEQ ID NO: 3; peptide number 25, residues 475-489 of SEQ ID NO: 3; peptide number 26, residues 476-490 of SEQ ID NO: 3; peptide number 27, residues 477-491 of SEQ ID NO: 3; peptide number 28, residues 478-492 of SEQ ID NO: 3; peptide number 29, residues 479-493 of SEQ ID NO: 3; peptide number 30, residues 480-494 of SEQ ID NO: 3; peptide number 31, residues 481-495 of SEQ ID NO: 3; peptide number 32, residues 482-496 of SEQ ID NO: 3; peptide number 33, residues 483-497 of SEQ ID NO: 3; peptide number 34, residues 484-498 of SEQ ID NO: 3; peptide number 35, residues 485-499 of SEQ ID NO: 3; peptide number 36, residues 486-500 of SEQ ID NO: 3; peptide number 37, residues 487-501 of SEQ ID NO: 3; peptide number 38, residues 488-502 of SEQ ID NO: 3; peptide number 38, residues 488-502 of SEQ ID NO: 3; peptide number 39, residues 489-503 of SEQ ID NO: 3; peptide number 40, residues 490-504 of SEQ ID NO: 3; peptide number 41, residues 491-505 of SEQ ID NO: 3; peptide number 42, residues 492-506 of SEQ ID NO: 3; peptide number 43, residues 493-507 of SEQ ID NO: 3; peptide number 44, residues 494-508 of SEQ ID NO: 3; peptide number 45, residues 495-509 of SEQ ID NO: 3; peptide number 46, residues 496-510 of SEQ ID NO: 3; peptide number 47, residues 497-511 of SEQ ID NO: 3; peptide number 48, residues 498-512 of SEQ ID NO: 3; peptide number 49, residues 499-513 of SEQ ID NO: 3; peptide number 50, residues 500-514 of SEQ ID NO: 3; peptide number 51, residues 501-515 of SEQ ID NO: 3; peptide number 52, residues 502-516 of SEQ ID NO: 3; peptide number 53, residues 503-517 of SEQ ID NO: 3; peptide number 54, residues 504-518 of SEQ ID NO: 3; peptide number 55, residues 505-519 of SEQ ID NO: 3; peptide number 56, residues 506-520 of SEQ ID NO: 3; peptide number 57, residues 507-521 of SEQ ID NO: 3; peptide number 58, residues 508-522 of SEQ ID NO: 3; peptide number 59, residues 509-523 of SEQ ID NO: 3; peptide number 60, residues 510-524 of SEQ ID NO: 3; peptide number 61, residues 511-525 of SEQ ID NO: 3; peptide number 62,
residues 512-526 of SEQ ID NO: 3; peptide number 63,
residues 513-527 of SEQ ID NO: 3; peptide number 64,
residues 514-528 of SEQ ID NO: 3; peptide number 65,
residues 515-529 of SEQ ID NO: 3; peptide number 66,
residues 516-530 of SEQ ID NO: 3; peptide number 67,
residues 517-531 of SEQ ID NO: 3; peptide number 68,
residues 518-532 of SEQ ID NO: 3; peptide number 69,
residues 519-533 of SEQ ID NO: 3; peptide number 70,
residues 520-534 of SEQ ID NO: 3; peptide number 71,
residues 521-535 of SEQ ID NO: 3; peptide number 72,
residues 522-536 of SEQ ID NO: 3; peptide number 73,
residues 523-537 of SEQ ID NO: 3; peptide number 74,
residues 524-538 of SEQ ID NO: 3; peptide number 75,
residues 525-539 of SEQ ID NO: 3; and peptide number 76,
residues 526-540 of SEQ ID NO: 3 (see also Table 1 for amino acid residues of each peptide).

Example 3: Identification of C1a-Derived Peptides that Block SNARE/Kv2.1 Interactions As described in Example 2, the C1a fragment corresponding to residues 411-522 of the rat Kv2.1 sequence (SEQ ID NO: 3) was capable of displacing syntaxin from Kv2.1, while the fragment corresponding to residues 411-472 was not. These findings narrowed down the syntaxin-binding region of Kv2.1's cytoplasmic tail to amino acid residues 472-522. To identify a minimal C1a peptide sequence capable of blocking SNARE/Kv2.1 interaction (and thereby capable of preventing the apoptotic K$^+$ current surge), C1a peptide fragments corresponding to this region and immediately adjacent regions (amino acids 451-540 of SEQ ID NO: 3; see FIG. 7, underlined sequence) were generated. A series of 76 overlapping peptides were synthesized. Each peptide was 15 amino acids in length and overlapped with 14 amino acids of each adjacent peptide. For example, the first peptide was ARSIEMMDIVVENKG (residues 451-465 of SEQ ID NO: 3), the second peptide was RSIEMMDIVVEN-KGE (residues 452-466 of SEQ ID NO: 3), the third peptide was SIEMMDIVVENKGE (residues 453-467 of SEQ ID NO: 3), and so on (see Table 1 below). The peptides were spot-plated as an array onto a polyvinylidene fluoride membrane using the SPOT-synthesis method as described in Brittain et al. (*Nat Med* 17:822, 2011). The membranes were incubated with a human syntaxin over-expressing CHO cell lysate and a far-Western analysis of syntaxin binding to the peptide arrays was performed using a commercially available syntaxin antibody and fluorescently tagged secondary antibody. Fluorescence intensity was quantified as an index of syntaxin binding to the spot array. As shown in FIG. 8, peptide #22 (residues 472-486 of SEQ ID NO: 3) was the initial peptide showing substantial binding, while peptide #28 (residues 478-492 of SEQ ID NO: 3) was the final peptide showing substantial binding. Based on these results, the overlapping peptide that represents the syntaxin-binding domain corresponds to the sequence HLSPNKWKW, set forth herein as SEQ ID NO: 9 (which corresponding to residues 478-486 of SEQ ID NO: 3; shown in bold underline in FIG. 7). A non-syntaxin-binding peptide (part of peptide #4) was picked at random (DIVVEEKNGE; residues 458-466 of SEQ ID NO: 3) to be used as a control in future studies.

The minimal binding sequence peptide (SEQ ID NO: 9) and the control peptide (residues 458-466 of SEQ ID NO: 3) were synthesized in larger quantities and coupled to the transduction domain of the HIV-1 TAT protein (YGRK-KRRQRRR; SEQ ID NO: 8) to generate cell-permeant TAT-Kv2.1c peptides. These peptides are tested for the capacity to bind syntaxin and displace syntaxin from Kv2.1, and can be further evaluated in electrophysiological, biochemical and neuroprotective studies (see Example 4).

TABLE 1

Kv2.1 Overlapping Peptides

| Peptide # | Residues of SEQ ID NO: 3 |
|---|---|
| 1 | 451-465 |
| 2 | 452-466 |
| 3 | 453-467 |
| 4 | 454-468 |
| 5 | 455-469 |
| 6 | 456-470 |
| 7 | 457-471 |
| 8 | 458-472 |
| 9 | 459-473 |
| 10 | 460-474 |
| 11 | 461-475 |
| 12 | 462-476 |
| 13 | 463-477 |
| 14 | 464-478 |
| 15 | 465-479 |
| 16 | 466-480 |
| 17 | 467-481 |
| 18 | 468-482 |
| 19 | 469-483 |
| 20 | 470-484 |
| 21 | 471-485 |
| 22 | 472-486 |
| 23 | 473-487 |
| 24 | 474-488 |
| 25 | 475-489 |
| 26 | 476-490 |
| 27 | 477-491 |
| 28 | 478-492 |
| 29 | 479-493 |
| 30 | 480-494 |
| 31 | 481-495 |
| 32 | 482-496 |
| 33 | 483-497 |
| 34 | 484-498 |
| 35 | 485-499 |
| 36 | 486-500 |
| 37 | 487-501 |
| 38 | 488-502 |
| 39 | 489-503 |
| 40 | 490-504 |
| 41 | 491-505 |
| 42 | 492-506 |
| 43 | 493-507 |
| 44 | 494-508 |
| 45 | 495-509 |
| 46 | 496-510 |
| 47 | 497-511 |
| 48 | 498-512 |
| 49 | 499-513 |
| 50 | 500-514 |
| 51 | 501-515 |
| 52 | 502-516 |
| 53 | 503-517 |
| 54 | 504-518 |
| 55 | 505-519 |
| 56 | 506-520 |
| 57 | 507-521 |
| 58 | 508-522 |
| 59 | 509-523 |

TABLE 1-continued

Kv2.1 Overlapping Peptides

| Peptide # | Residues of SEQ ID NO: 3 |
|---|---|
| 60 | 510-524 |
| 61 | 511-525 |
| 62 | 512-526 |
| 63 | 513-527 |
| 64 | 514-528 |
| 65 | 515-529 |
| 66 | 516-530 |
| 67 | 517-531 |
| 68 | 518-532 |
| 69 | 519-533 |
| 70 | 520-534 |
| 71 | 521-535 |
| 72 | 522-536 |
| 73 | 523-537 |
| 74 | 524-538 |
| 75 | 525-539 |
| 76 | 526-540 |

Example 4: Characterization of C1a-derived Peptides that Block SNARE/Kv2.1 Interactions TAT-Kv2.1c peptides capable of displacing syntaxin from Kv2.1 are tested for their ability to block cell death in cultured neurons exposed to injurious conditions known to be accompanied by a K$^+$ current surge, including oxygen-glucose deprivation.

In addition, a middle cerebral artery occlusion (MCAO) mouse model is used to assess the neuroprotective role of TAT-linked C1a-derived peptides in vivo. Male mice (approximately 25 g) are anesthetized, the left common carotid artery is exposed and the occipital artery branches of the external carotid artery are isolated and coagulated. The internal carotid artery is isolated, with the extra cranial branches dissected and ligated. A No. 6-0 nylon suture is introduced into the lumen of the external carotid artery, advanced into the middle cerebral artery until reduction of regional cerebral blood flow is observed with a laser Doppler probe fixed over the core area supplied by the MCA, left in this position for 1 hour and then withdrawn. Temperature is maintained at 37° C. throughout the experiment and during post-surgical recovery using a temperature-controlled recirculating water blanket. Blood pressure and blood samples are accessed through femoral artery cannulation. Blood pressure is continuously monitored. Blood samples (maximum volume 0.2 ml/experiment) are drawn to determine blood glucose, PaO$_2$, PaCO$_2$ and pH once before and following ischemia. Assessment of brain infarct volume is performed 48 hours later by 2,3,5-triphenyltetrazolium chloride monohydrate (TTC) staining of 2 mm coronal slices using ImageJ software, correcting for edema and normalized to contralateral hemisphere. Drug treatment and image analysis are done by a double-blinded procedure.

TAT-linked C1a derived peptides capable of displacing syntaxin from Kv2.1 are tested in this model. The peptides are administered intravenously in saline, at two doses. Peptides are administered 1 hour prior to MCAO (pre-treatment), 15 minutes prior to reperfusion and 1 hour after reperfusion.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

---

The invention claimed is:

1. A fusion protein, comprising:
a polypeptide comprising at least 8 consecutive amino acids of SEQ ID NO: 9, wherein the polypeptide is no more than 20 amino acids in length and shares at least 90% sequence identity with the Kv2.1 polypeptide sequence of SEQ ID NO: 7; and
a heterologous protein.

2. The fusion protein of claim 1, wherein the polypeptide is 10 to 15 amino acids in length.

3. The fusion protein of claim 1, wherein the polypeptide shares at least 90% sequence identity with the Kv2.1 polypeptide sequence of SEQ ID NO: 2, SEQ ID NO: 4 or SEQ ID NO: 6.

4. The fusion protein of claim 1, wherein the polypeptide comprises the amino acid sequence of SEQ ID NO: 9.

5. The fusion protein of claim 1, wherein the polypeptide consists of the amino acid sequence of SEQ ID NO: 9.

6. The fusion protein of claim 1, wherein the heterologous protein comprises a cell-penetrating peptide (CPP).

7. The fusion protein of claim 6, wherein the CPP is the TAT peptide comprising the amino acid sequence of SEQ ID NO: 8.

8. A composition comprising the fusion protein of claim 1 and a pharmaceutically acceptable carrier.

9. A method of inhibiting binding of syntaxin to Kv2.1 in a cell, comprising contacting the cell with the fusion protein of claim 1.

10. The method of claim 9, wherein the method is an in vitro method.

11. The method of claim 9, wherein the method is an in vivo method and contacting the cell with the fusion protein comprises administering the fusion protein to a subject.

12. The method of claim 11, wherein the subject is suffering from or has suffered from cerebral ischemia, stroke, traumatic brain injury or a neurodegenerative disease.

13. A method of inhibiting neuronal damage in a subject, comprising administering to the subject the fusion protein of claim 1.

14. The fusion protein of claim 1, wherein the polypeptide shares at least 95% sequence identity with the Kv2.1 polypeptide sequence of SEQ ID NO: 2, SEQ ID NO: 4 or SEQ ID NO: 6.

15. An isolated nucleic acid molecule encoding a fusion protein, comprising
a polypeptide comprising at least 8 consecutive amino acids of SEQ ID NO: 9, wherein the polypeptide is no more than 20 amino acids in length and shares at least 90% sequence identity with the Kv2.1 polypeptide sequence of SEQ ID NO: 7; and
a heterologous protein.

16. The isolated nucleic acid molecule of claim 15, operably linked to a heterologous promoter.

17. A vector comprising the isolated nucleic acid molecule of claim 16.

18. A method of inhibiting binding of syntaxin to Kv2.1 in a cell, comprising contacting the cell with a recombinant polypeptide comprising at least 8 consecutive amino acids of SEQ ID NO: 9, wherein the polypeptide is no more than 20 amino acids in length and shares at least 90% sequence identity with the Kv2.1 polypeptide sequence of SEQ ID NO: 7.

19. A method of inhibiting neuronal damage in a subject, comprising administering to the subject a recombinant polypeptide comprising at least 8 consecutive amino acids of SEQ ID NO: 9, wherein the polypeptide is no more than 20 amino acids in length and shares at least 90% sequence identity with the Kv2.1 polypeptide sequence of SEQ ID NO: 7.

20. A vector comprising an isolated nucleic acid molecule encoding a recombinant polypeptide comprising at least 8 consecutive amino acids of SEQ ID NO: 9, wherein the polypeptide is no more than 20 amino acids in length and shares at least 90% sequence identity with the Kv2.1 polypeptide sequence of SEQ ID NO: 7, and wherein the nucleic acid molecule is operably linked to a heterologous promoter.

* * * * *

SEQUENCE LISTING

```
<160> NUMBER OF SEQ ID NOS: 9

<210> SEQ ID NO 1
<211> LENGTH: 858
<212> TYPE: PRT
<213> ORGANISM: Homo sapiens

<400> SEQUENCE: 1

Met Pro Ala Gly Met Thr Lys His Gly Ser Arg Ser Thr Ser Ser Leu
1               5                   10                  15

Pro Pro Glu Pro Met Glu Ile Val Arg Ser Lys Ala Cys Ser Arg Arg
            20                  25                  30

Val Arg Leu Asn Val Gly Gly Leu Ala His Glu Val Leu Trp Arg Thr
        35                  40                  45

Leu Asp Arg Leu Pro Arg Thr Arg Leu Gly Lys Leu Arg Asp Cys Asn
    50                  55                  60

Thr His Asp Ser Leu Leu Glu Val Cys Asp Asp Tyr Ser Leu Asp Asp
65                  70                  75                  80

Asn Glu Tyr Phe Phe Asp Arg His Pro Gly Ala Phe Thr Ser Ile Leu
                85                  90                  95

Asn Phe Tyr Arg Thr Gly Arg Leu His Met Met Glu Glu Met Cys Ala
            100                 105                 110

Leu Ser Phe Ser Gln Glu Leu Asp Tyr Trp Gly Ile Asp Glu Ile Tyr
        115                 120                 125
```

-continued

```
Leu Glu Ser Cys Cys Gln Ala Arg Tyr His Gln Lys Lys Glu Gln Met
    130                 135                 140
Asn Glu Glu Leu Lys Arg Glu Ala Glu Thr Leu Arg Glu Arg Glu Gly
145                 150                 155                 160
Glu Glu Phe Asp Asn Thr Cys Cys Ala Glu Lys Arg Lys Lys Leu Trp
                165                 170                 175
Asp Leu Leu Glu Lys Pro Asn Ser Ser Val Ala Ala Lys Ile Leu Ala
            180                 185                 190
Ile Ile Ser Ile Met Phe Ile Val Leu Ser Thr Ile Ala Leu Ser Leu
        195                 200                 205
Asn Thr Leu Pro Glu Leu Gln Ser Leu Asp Glu Phe Gly Gln Ser Thr
210                 215                 220
Asp Asn Pro Gln Leu Ala His Val Glu Ala Val Cys Ile Ala Trp Phe
225                 230                 235                 240
Thr Met Glu Tyr Leu Leu Arg Phe Leu Ser Ser Pro Lys Lys Trp Lys
                245                 250                 255
Phe Phe Lys Gly Pro Leu Asn Ala Ile Asp Leu Leu Ala Ile Leu Pro
            260                 265                 270
Tyr Tyr Val Thr Ile Phe Leu Thr Glu Ser Asn Lys Ser Val Leu Gln
        275                 280                 285
Phe Gln Asn Val Arg Arg Val Val Gln Ile Phe Arg Ile Met Arg Ile
    290                 295                 300
Leu Arg Ile Leu Lys Leu Ala Arg His Ser Thr Gly Leu Gln Ser Leu
305                 310                 315                 320
Gly Phe Thr Leu Arg Arg Ser Tyr Asn Glu Leu Gly Leu Leu Ile Leu
                325                 330                 335
Phe Leu Ala Met Gly Ile Met Ile Phe Ser Ser Leu Val Phe Phe Ala
            340                 345                 350
Glu Lys Asp Glu Asp Thr Lys Phe Lys Ser Ile Pro Ala Ser Phe
        355                 360                 365
Trp Trp Ala Thr Ile Thr Met Thr Thr Val Gly Tyr Gly Asp Ile Tyr
    370                 375                 380
Pro Lys Thr Leu Leu Gly Lys Ile Val Gly Gly Leu Cys Cys Ile Ala
385                 390                 395                 400
Gly Val Leu Val Ile Ala Leu Pro Ile Pro Ile Ile Val Asn Asn Phe
                405                 410                 415
Ser Glu Phe Tyr Lys Glu Gln Lys Arg Gln Glu Lys Ala Ile Lys Arg
            420                 425                 430
Arg Glu Ala Leu Glu Arg Ala Lys Arg Asn Gly Ser Ile Val Ser Met
        435                 440                 445
Asn Met Lys Asp Ala Phe Ala Arg Ser Ile Glu Met Met Asp Ile Val
    450                 455                 460
Val Glu Lys Asn Gly Glu Asn Met Gly Lys Lys Asp Lys Val Gln Asp
465                 470                 475                 480
Asn His Leu Ser Pro Asn Lys Trp Lys Trp Thr Lys Arg Thr Leu Ser
                485                 490                 495
Glu Thr Ser Ser Ser Lys Ser Phe Glu Thr Lys Glu Gln Gly Ser Pro
            500                 505                 510
Glu Lys Ala Arg Ser Ser Ser Pro Gln His Leu Asn Val Gln Gln
        515                 520                 525
Leu Glu Asp Met Tyr Asn Lys Met Ala Lys Thr Gln Ser Gln Pro Ile
    530                 535                 540
Leu Asn Thr Lys Glu Ser Ala Ala Gln Ser Lys Pro Lys Glu Glu Leu
```

```
                545                 550                 555                 560
Glu Met Glu Ser Ile Pro Ser Pro Val Ala Pro Leu Pro Thr Arg Thr
                    565                 570                 575
Glu Gly Val Ile Asp Met Arg Ser Met Ser Ser Ile Asp Ser Phe Ile
                580                 585                 590
Ser Cys Ala Thr Asp Phe Pro Glu Ala Thr Arg Phe Ser His Ser Pro
            595                 600                 605
Leu Thr Ser Leu Pro Ser Lys Thr Gly Gly Ser Thr Ala Pro Glu Val
        610                 615                 620
Gly Trp Arg Gly Ala Leu Gly Ala Ser Gly Gly Arg Phe Val Glu Ala
625                 630                 635                 640
Asn Pro Ser Pro Asp Ala Ser Gln His Ser Ser Phe Phe Ile Glu Ser
                645                 650                 655
Pro Lys Ser Ser Met Lys Thr Asn Asn Pro Leu Lys Leu Arg Ala Leu
            660                 665                 670
Lys Val Asn Phe Met Glu Gly Asp Pro Ser Pro Leu Leu Pro Val Leu
        675                 680                 685
Gly Met Tyr His Asp Pro Leu Arg Asn Arg Gly Ser Ala Ala Ala Ala
        690                 695                 700
Val Ala Gly Leu Glu Cys Ala Thr Leu Leu Asp Lys Ala Val Leu Ser
705                 710                 715                 720
Pro Glu Ser Ser Ile Tyr Thr Thr Ala Ser Ala Lys Thr Pro Pro Arg
                725                 730                 735
Ser Pro Glu Lys His Thr Ala Ile Ala Phe Asn Phe Glu Ala Gly Val
            740                 745                 750
His Gln Tyr Ile Asp Ala Asp Thr Asp Asp Glu Gly Gln Leu Leu Tyr
        755                 760                 765
Ser Val Asp Ser Ser Pro Pro Lys Ser Leu Pro Gly Ser Thr Ser Pro
        770                 775                 780
Lys Phe Ser Thr Gly Thr Arg Ser Glu Lys Asn His Phe Glu Ser Ser
785                 790                 795                 800
Pro Leu Pro Thr Ser Pro Lys Phe Leu Arg Gln Asn Cys Ile Tyr Ser
                805                 810                 815
Thr Glu Ala Leu Thr Gly Lys Gly Pro Ser Gly Gln Glu Lys Cys Lys
            820                 825                 830
Leu Glu Asn His Ile Ser Pro Asp Val Arg Val Leu Pro Gly Gly Gly
        835                 840                 845
Ala His Gly Ser Thr Arg Asp Gln Ser Ile
    850                 855

<210> SEQ ID NO 2
<211> LENGTH: 112
<212> TYPE: PRT
<213> ORGANISM: Homo sapiens

<400> SEQUENCE: 2

Asn Phe Ser Glu Phe Tyr Lys Glu Gln Lys Arg Gln Glu Lys Ala Ile
1               5                   10                  15
Lys Arg Arg Glu Ala Leu Glu Arg Ala Lys Arg Asn Gly Ser Ile Val
                20                  25                  30
Ser Met Asn Met Lys Asp Ala Phe Ala Arg Ser Ile Glu Met Met Asp
            35                  40                  45
Ile Val Val Glu Lys Asn Gly Glu Asn Met Gly Lys Lys Asp Lys Val
        50                  55                  60
```

-continued

Gln Asp Asn His Leu Ser Pro Asn Lys Trp Lys Trp Thr Lys Arg Thr
 65                  70                  75                  80

Leu Ser Glu Thr Ser Ser Ser Lys Ser Phe Glu Thr Lys Glu Gln Gly
                 85                  90                  95

Ser Pro Glu Lys Ala Arg Ser Ser Ser Pro Gln His Leu Asn Val
            100                 105                 110

<210> SEQ ID NO 3
<211> LENGTH: 853
<212> TYPE: PRT
<213> ORGANISM: Rattus norvegicus

<400> SEQUENCE: 3

Met Thr Lys His Gly Ser Arg Ser Thr Ser Ser Leu Pro Pro Glu Pro
1               5                   10                  15

Met Glu Ile Val Arg Ser Lys Ala Cys Ser Arg Val Arg Leu Asn
            20                  25                  30

Val Gly Gly Leu Ala His Glu Val Leu Trp Arg Thr Leu Asp Arg Leu
             35                  40                  45

Pro Arg Thr Arg Leu Gly Lys Leu Arg Asp Cys Asn Thr His Asp Ser
 50                  55                  60

Leu Leu Gln Val Cys Asp Asp Tyr Ser Leu Glu Asp Asn Glu Tyr Phe
 65                  70                  75                  80

Phe Asp Arg His Pro Gly Ala Phe Thr Ser Ile Leu Asn Phe Tyr Arg
                 85                  90                  95

Thr Gly Arg Leu His Met Met Glu Glu Met Cys Ala Leu Ser Phe Ser
            100                 105                 110

Gln Glu Leu Asp Tyr Trp Gly Ile Asp Glu Ile Tyr Leu Glu Ser Cys
        115                 120                 125

Cys Gln Ala Arg Tyr His Gln Lys Lys Glu Gln Met Asn Glu Glu Leu
    130                 135                 140

Lys Arg Glu Ala Glu Thr Leu Arg Glu Arg Glu Gly Glu Glu Phe Asp
145                 150                 155                 160

Asn Thr Cys Cys Ala Glu Lys Arg Lys Leu Trp Asp Leu Leu Glu
                165                 170                 175

Lys Pro Asn Ser Ser Val Ala Ala Lys Ile Leu Ala Ile Ile Ser Ile
            180                 185                 190

Met Phe Ile Val Leu Ser Thr Ile Ala Leu Ser Leu Asn Thr Leu Pro
        195                 200                 205

Glu Leu Gln Ser Leu Asp Glu Phe Gly Gln Ser Thr Asp Asn Pro Gln
    210                 215                 220

Leu Ala His Val Glu Ala Val Cys Ile Ala Trp Phe Thr Met Glu Tyr
225                 230                 235                 240

Leu Leu Arg Phe Leu Ser Ser Pro Lys Lys Trp Lys Phe Phe Lys Gly
                245                 250                 255

Pro Leu Asn Ala Ile Asp Leu Leu Ala Ile Leu Pro Tyr Tyr Val Thr
            260                 265                 270

Ile Phe Leu Thr Glu Ser Asn Lys Ser Val Leu Gln Phe Gln Asn Val
        275                 280                 285

Arg Arg Val Val Gln Ile Phe Arg Ile Met Arg Ile Leu Arg Ile Leu
    290                 295                 300

Lys Leu Ala Arg His Ser Thr Gly Leu Gln Ser Leu Gly Phe Thr Leu
305                 310                 315                 320

Arg Arg Ser Tyr Asn Glu Leu Gly Leu Leu Ile Leu Phe Leu Ala Met
                325                 330                 335

```
Gly Ile Met Ile Phe Ser Ser Leu Val Phe Ala Glu Lys Asp Glu
            340                 345                 350

Asp Asp Thr Lys Phe Lys Ser Ile Pro Ala Ser Phe Trp Ala Thr
            355                 360                 365

Ile Thr Met Thr Thr Val Gly Tyr Gly Asp Ile Tyr Pro Lys Thr Leu
    370                 375                 380

Leu Gly Lys Ile Val Gly Leu Cys Cys Ile Ala Gly Val Leu Val
385                 390                 395                 400

Ile Ala Leu Pro Ile Pro Ile Val Asn Asn Phe Ser Glu Phe Tyr
            405                 410                 415

Lys Glu Gln Lys Arg Gln Glu Lys Ala Ile Lys Arg Glu Ala Leu
            420                 425                 430

Glu Arg Ala Lys Arg Asn Gly Ser Ile Val Ser Met Asn Met Lys Asp
            435                 440                 445

Ala Phe Ala Arg Ser Ile Glu Met Met Asp Ile Val Val Glu Lys Asn
            450                 455                 460

Gly Glu Ser Ile Ala Lys Lys Asp Lys Val Gln Asp Asn His Leu Ser
465                 470                 475                 480

Pro Asn Lys Trp Lys Trp Thr Lys Arg Ala Leu Ser Glu Thr Ser Ser
                485                 490                 495

Ser Lys Ser Phe Glu Thr Lys Glu Gln Gly Ser Pro Glu Lys Ala Arg
            500                 505                 510

Ser Ser Ser Ser Pro Gln His Leu Asn Val Gln Gln Leu Glu Asp Met
            515                 520                 525

Tyr Ser Lys Met Ala Lys Thr Gln Ser Gln Pro Ile Leu Asn Thr Lys
            530                 535                 540

Glu Met Ala Pro Gln Ser Lys Pro Pro Glu Glu Leu Glu Met Ser Ser
545                 550                 555                 560

Met Pro Ser Pro Val Ala Pro Leu Pro Ala Arg Thr Glu Gly Val Ile
                565                 570                 575

Asp Met Arg Ser Met Ser Ser Ile Asp Ser Phe Ile Ser Cys Ala Thr
            580                 585                 590

Asp Phe Pro Glu Ala Thr Arg Phe Ser His Ser Pro Leu Ala Ser Leu
            595                 600                 605

Ser Ser Lys Ala Gly Ser Ser Thr Ala Pro Glu Val Gly Trp Arg Gly
    610                 615                 620

Ala Leu Gly Ala Ser Gly Gly Arg Leu Thr Glu Thr Asn Pro Ile Pro
625                 630                 635                 640

Glu Thr Ser Arg Ser Gly Phe Phe Val Glu Ser Pro Arg Ser Ser Met
                645                 650                 655

Lys Thr Asn Asn Pro Leu Lys Leu Arg Ala Leu Lys Val Asn Phe Val
            660                 665                 670

Glu Gly Asp Pro Thr Pro Leu Leu Pro Ser Leu Gly Leu Tyr His Asp
            675                 680                 685

Pro Leu Arg Asn Arg Gly Gly Ala Ala Ala Val Ala Gly Leu Glu
            690                 695                 700

Cys Ala Ser Leu Leu Asp Lys Pro Val Leu Ser Pro Glu Ser Ser Ile
705                 710                 715                 720

Tyr Thr Thr Ala Ser Ala Arg Thr Pro Pro Arg Ser Pro Glu Lys His
            725                 730                 735

Thr Ala Ile Ala Phe Asn Phe Glu Ala Gly Val His Gln Tyr Ile Asp
            740                 745                 750
```

Thr Asp Thr Asp Asp Glu Gly Gln Leu Leu Tyr Ser Val Asp Ser Ser
            755                 760                 765

Pro Pro Lys Ser Leu His Gly Ser Thr Ser Pro Lys Phe Ser Thr Gly
    770                 775                 780

Ala Arg Thr Glu Lys Asn His Phe Glu Ser Ser Pro Leu Pro Thr Ser
785                 790                 795                 800

Pro Lys Phe Leu Arg Pro Asn Cys Val Tyr Ser Ser Glu Gly Leu Thr
                805                 810                 815

Gly Lys Gly Pro Gly Ala Gln Glu Lys Cys Lys Leu Glu Asn His Thr
            820                 825                 830

Pro Pro Asp Val His Met Leu Pro Gly Gly Gly Ala His Gly Ser Thr
        835                 840                 845

Arg Asp Gln Ser Ile
    850

<210> SEQ ID NO 4
<211> LENGTH: 112
<212> TYPE: PRT
<213> ORGANISM: Rattus norvegicus

<400> SEQUENCE: 4

Asn Phe Ser Glu Phe Tyr Lys Glu Gln Lys Arg Gln Glu Lys Ala Ile
1               5                   10                  15

Lys Arg Arg Glu Ala Leu Glu Arg Ala Lys Arg Asn Gly Ser Ile Val
            20                  25                  30

Ser Met Asn Met Lys Asp Ala Phe Ala Arg Ser Ile Glu Met Met Asp
        35                  40                  45

Ile Val Val Glu Lys Asn Gly Glu Ser Ile Ala Lys Lys Asp Lys Val
    50                  55                  60

Gln Asp Asn His Leu Ser Pro Asn Lys Trp Lys Trp Thr Lys Arg Ala
65                  70                  75                  80

Leu Ser Glu Thr Ser Ser Ser Lys Ser Phe Glu Thr Lys Glu Gln Gly
                85                  90                  95

Ser Pro Glu Lys Ala Arg Ser Ser Ser Pro Gln His Leu Asn Val
            100                 105                 110

<210> SEQ ID NO 5
<211> LENGTH: 857
<212> TYPE: PRT
<213> ORGANISM: Mus musculus

<400> SEQUENCE: 5

Met Pro Ala Gly Met Thr Lys His Gly Ser Arg Ser Thr Ser Ser Leu
1               5                   10                  15

Pro Pro Glu Pro Met Glu Ile Val Arg Ser Lys Ala Cys Ser Arg Arg
            20                  25                  30

Val Arg Leu Asn Val Gly Gly Leu Ala His Glu Val Leu Trp Arg Thr
        35                  40                  45

Leu Asp Arg Leu Pro Arg Thr Arg Leu Gly Lys Leu Arg Asp Cys Asn
    50                  55                  60

Thr His Asp Ser Leu Leu Gln Val Cys Asp Asp Tyr Ser Leu Glu Asp
65                  70                  75                  80

Asn Glu Tyr Phe Phe Asp Arg His Pro Gly Ala Phe Thr Ser Ile Leu
                85                  90                  95

Asn Phe Tyr Arg Thr Gly Arg Leu His Met Met Glu Glu Met Cys Ala
            100                 105                 110

-continued

```
Leu Ser Phe Ser Gln Glu Leu Asp Tyr Trp Gly Ile Asp Glu Ile Tyr
            115                 120                 125
Leu Glu Ser Cys Cys Gln Ala Arg Tyr His Lys Lys Glu Gln Met
    130                 135                 140
Asn Glu Glu Leu Lys Arg Glu Ala Glu Thr Leu Arg Glu Arg Glu Gly
145                 150                 155                 160
Glu Glu Phe Asp Asn Thr Cys Cys Ala Glu Lys Arg Lys Lys Leu Trp
                165                 170                 175
Asp Leu Leu Glu Lys Pro Asn Ser Ser Val Ala Ala Lys Ile Leu Ala
            180                 185                 190
Ile Ile Ser Ile Met Phe Ile Val Leu Ser Thr Ile Ala Leu Ser Leu
            195                 200                 205
Asn Thr Leu Pro Glu Leu Gln Ser Leu Asp Glu Phe Gly Gln Ser Thr
210                 215                 220
Asp Asn Pro Gln Leu Ala His Val Glu Ala Val Cys Ile Ala Trp Phe
225                 230                 235                 240
Thr Met Glu Tyr Leu Leu Arg Phe Leu Ser Ser Pro Lys Lys Trp Lys
                245                 250                 255
Phe Phe Lys Gly Pro Leu Asn Ala Ile Asp Leu Leu Ala Ile Leu Pro
            260                 265                 270
Tyr Tyr Val Thr Ile Phe Leu Thr Glu Ser Asn Lys Ser Val Leu Gln
            275                 280                 285
Phe Gln Asn Val Arg Arg Val Gln Ile Phe Arg Ile Met Arg Ile
    290                 295                 300
Leu Arg Ile Leu Lys Leu Ala Arg His Ser Thr Gly Leu Gln Ser Leu
305                 310                 315                 320
Gly Phe Thr Leu Arg Arg Ser Tyr Asn Glu Leu Gly Leu Leu Ile Leu
                325                 330                 335
Phe Leu Ala Met Gly Ile Met Ile Phe Ser Ser Leu Val Phe Phe Ala
            340                 345                 350
Glu Lys Asp Glu Asp Thr Lys Phe Lys Ser Ile Pro Ala Ser Phe
            355                 360                 365
Trp Trp Ala Thr Ile Thr Met Thr Thr Val Gly Tyr Gly Asp Ile Tyr
370                 375                 380
Pro Lys Thr Leu Leu Gly Lys Ile Val Gly Gly Leu Cys Cys Ile Ala
385                 390                 395                 400
Gly Val Leu Val Ile Ala Leu Pro Ile Pro Ile Val Asn Asn Phe
                405                 410                 415
Ser Glu Phe Tyr Lys Glu Gln Lys Arg Gln Glu Lys Ala Ile Lys Arg
            420                 425                 430
Arg Glu Ala Leu Glu Arg Ala Lys Arg Asn Gly Ser Ile Val Ser Met
            435                 440                 445
Asn Met Lys Asp Ala Phe Ala Arg Ser Ile Glu Met Met Asp Ile Val
    450                 455                 460
Val Glu Lys Asn Gly Glu Gly Val Ala Lys Lys Asp Lys Val Gln Asp
465                 470                 475                 480
Asn His Leu Ser Pro Asn Lys Trp Lys Trp Thr Lys Arg Ala Leu Ser
                485                 490                 495
Glu Thr Ser Ser Lys Ser Phe Glu Thr Lys Glu Gln Gly Ser Pro
            500                 505                 510
Glu Lys Ala Arg Ser Ser Ser Pro Gln His Leu Asn Val Gln Gln
            515                 520                 525
Leu Gln Asp Met Tyr Ser Lys Met Ala Lys Thr Gln Ser Gln Pro Ile
```

```
                      530                 535                 540
Leu Asn Thr Lys Glu Met Ala Pro Gln Ser Gln Pro Gln Glu Glu Leu
545                 550                 555                 560

Glu Met Gly Ser Met Pro Ser Pro Val Ala Pro Leu Pro Thr Arg Thr
                565                 570                 575

Glu Gly Val Ile Asp Met Arg Ser Met Ser Ser Ile Asp Ser Phe Ile
            580                 585                 590

Ser Cys Ala Thr Asp Phe Pro Glu Ala Thr Arg Phe Ser His Ser Pro
        595                 600                 605

Leu Ala Ser Leu Ser Gly Lys Ser Gly Gly Ser Thr Ala Pro Glu Val
    610                 615                 620

Gly Trp Arg Gly Ala Leu Gly Ala Ser Gly Gly Arg Leu Met Glu Thr
625                 630                 635                 640

Asn Pro Ile Pro Glu Ala Ser Arg Ser Gly Phe Phe Val Glu Ser Pro
                645                 650                 655

Arg Ser Ser Met Lys Thr His Asn Pro Met Lys Leu Arg Ala Leu Lys
                660                 665                 670

Val Asn Phe Leu Glu Gly Asp Pro Thr Pro Leu Leu Pro Ala Leu Gly
            675                 680                 685

Leu Tyr His Asp Pro Leu Arg Asn Arg Gly Gly Ala Ala Ala Ala Val
        690                 695                 700

Ala Gly Leu Glu Cys Ala Ser Leu Leu Asp Lys Pro Val Leu Ser Pro
705                 710                 715                 720

Glu Ser Ser Ile Tyr Thr Thr Ala Ser Ala Arg Thr Pro Pro Arg Ser
                725                 730                 735

Pro Glu Lys His Thr Ala Ile Ala Phe Asn Phe Glu Ala Gly Val His
                740                 745                 750

Gln Tyr Ile Asp Thr Asp Thr Asp Asp Glu Gly Gln Leu Leu Tyr Ser
            755                 760                 765

Val Asp Ser Ser Pro Pro Lys Ser Leu His Gly Ser Thr Ser Pro Lys
    770                 775                 780

Phe Ser Leu Gly Ala Arg Thr Glu Lys Asn His Phe Glu Ser Ser Pro
785                 790                 795                 800

Leu Pro Thr Ser Pro Lys Phe Leu Arg Pro Asn Cys Val Tyr Ala Ser
                805                 810                 815

Glu Gly Leu Pro Gly Lys Gly Pro Gly Ala Gln Glu Lys Cys Lys Leu
                820                 825                 830

Glu Asn His Thr Ser Pro Asp Val His Met Leu Pro Gly Gly Gly Ala
            835                 840                 845

His Gly Ser Thr Arg Asp Gln Ser Ile
850                 855

<210> SEQ ID NO 6
<211> LENGTH: 112
<212> TYPE: PRT
<213> ORGANISM: Mus musculus

<400> SEQUENCE: 6

Asn Phe Ser Glu Phe Tyr Lys Glu Gln Lys Arg Gln Glu Lys Ala Ile
1               5                   10                  15

Lys Arg Arg Glu Ala Leu Glu Arg Ala Lys Arg Asn Gly Ser Ile Val
            20                  25                  30

Ser Met Asn Met Lys Asp Ala Phe Ala Arg Ser Ile Glu Met Met Asp
        35                  40                  45
```

```
Ile Val Val Glu Lys Asn Gly Glu Gly Val Ala Lys Lys Asp Lys Val
        50                  55                  60

Gln Asp Asn His Leu Ser Pro Asn Lys Trp Lys Trp Thr Lys Arg Ala
 65                  70                  75                  80

Leu Ser Glu Thr Ser Ser Ser Lys Ser Phe Glu Thr Lys Glu Gln Gly
                 85                  90                  95

Ser Pro Glu Lys Ala Arg Ser Ser Ser Pro Gln His Leu Asn Val
            100                 105                 110

<210> SEQ ID NO 7
<211> LENGTH: 112
<212> TYPE: PRT
<213> ORGANISM: Artificial Sequence
<220> FEATURE:
<223> OTHER INFORMATION: Synthetic peptide (human, rat, mouse consensus
      sequence)
<220> FEATURE:
<221> NAME/KEY: MISC_FEATURE
<222> LOCATION: (57)..(57)
<223> OTHER INFORMATION: Xaa = Asn, Ser or Gly
<220> FEATURE:
<221> NAME/KEY: MISC_FEATURE
<222> LOCATION: (58)..(58)
<223> OTHER INFORMATION: Xaa = Met, Ile or Val
<220> FEATURE:
<221> NAME/KEY: MISC_FEATURE
<222> LOCATION: (59)..(59)
<223> OTHER INFORMATION: Xaa = Gly or Ala
<220> FEATURE:
<221> NAME/KEY: MISC_FEATURE
<222> LOCATION: (80)..(80)
<223> OTHER INFORMATION: Xaa = Thr or Ala

<400> SEQUENCE: 7

Asn Phe Ser Glu Phe Tyr Lys Glu Gln Lys Arg Gln Glu Lys Ala Ile
  1               5                  10                  15

Lys Arg Arg Glu Ala Leu Glu Arg Ala Lys Arg Asn Gly Ser Ile Val
             20                  25                  30

Ser Met Asn Met Lys Asp Ala Phe Ala Arg Ser Ile Glu Met Met Asp
         35                  40                  45

Ile Val Val Glu Lys Asn Gly Glu Xaa Xaa Xaa Lys Lys Asp Lys Val
        50                  55                  60

Gln Asp Asn His Leu Ser Pro Asn Lys Trp Lys Trp Thr Lys Arg Xaa
 65                  70                  75                  80

Leu Ser Glu Thr Ser Ser Ser Lys Ser Phe Glu Thr Lys Glu Gln Gly
                 85                  90                  95

Ser Pro Glu Lys Ala Arg Ser Ser Ser Pro Gln His Leu Asn Val
            100                 105                 110

<210> SEQ ID NO 8
<211> LENGTH: 11
<212> TYPE: PRT
<213> ORGANISM: Human immunodeficiency virus

<400> SEQUENCE: 8

Tyr Gly Arg Lys Lys Arg Arg Gln Arg Arg
 1               5                  10

<210> SEQ ID NO 9
<211> LENGTH: 9
<212> TYPE: PRT
<213> ORGANISM: Rattus norvegicus
```

<400> SEQUENCE: 9

His Leu Ser Pro Asn Lys Trp Lys Trp
1               5